United States Patent [19]
Higashikawa et al.

[11] Patent Number: 5,851,200
[45] Date of Patent: *Dec. 22, 1998

[54] SYRINGE, ITS SEALING STRUCTURE AND SEALING METHOD AND SLIDING VALVE FOR SYRINGE

[75] Inventors: Tetsuro Higashikawa; Hirokazu Suzuki, both of Tokyo, Japan

[73] Assignee: Tetsuro Higashikawa, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 765,902

[22] PCT Filed: Dec. 27, 1995

[86] PCT No.: PCT/JP95/02728

§ 371 Date: Jan. 7, 1997

§ 102(e) Date: Jan. 7, 1997

[87] PCT Pub. No.: WO97/05916

PCT Pub. Date: Feb. 20, 1997

[30]     Foreign Application Priority Data

Aug. 9, 1995  [JP]  Japan .................................. 7-203352
Aug. 17, 1995 [JP]  Japan .................................. 7-209410

[51] Int. Cl.⁶ ............................................... A61M 5/00
[52] U.S. Cl. ........................ 604/199; 604/111; 604/187
[58] Field of Search ................................. 604/111, 110, 604/187, 199, 49

[56]              References Cited

U.S. PATENT DOCUMENTS 4,475,903 10/1984 Stenhuisen et al. ..................... 604/111
4,929,230  5/1990 Pfleger .
5,205,827  4/1993 Novacek et al. ..................... 604/111 X

FOREIGN PATENT DOCUMENTS 47-10446  5/1972  Japan .
49-87491  8/1974  Japan .
50-43789  4/1975  Japan .
60-6532   1/1985  Japan .
3-250664 10/1991  Japan .
6-335654 12/1994  Japan .
7-000511  1/1995  Japan .

*Primary Examiner*—John D. Yasko
*Attorney, Agent, or Firm*—McDermott, Will & Emery

[57]              ABSTRACT

As a sealing structure for a syringe, a waterproofing film is adhered to the surface of a cap (6), a barrel (3) and a cylinder body (2) to cover fitting areas therebetween. The film is made of synthetic resin having a melting point higher than the temperature of flowing water vapor in post sterilization.

As a sliding valve for a syringe, an inclined lip (24) is continuously protruded from the outer surface of a short cylindrical body (22). At the one end of the body, an annular lip (23) is formed. The inclined lip has a recess (34) for introducing a medicine liquid. The inclined lip may be formed in plural pairs of inverted ɪᴠ, in plural stages, in plural strips in an axial direction, or in a shape to cross to form a sea slug wall. The sliding valve can be inserted with no inclination so that stagnant of air is not produced.

As a syringe, at the tip of a cylinder, a bulging portion (87) having a larger inner diameter than that of the cylinder is formed integrally to the cylinder and the inner diameter of said bulging portion is larger than the outer diameter of an elastic sliding valve so that a medicine liquid is discharged through a gap on the outside. On the bottom wall of said bulging portion, a protrusion (94) for supporting said sliding valve is formed to form a gap on the bottom. The sliding valve (90) includes a body (101) having a smaller diameter than the inner diameter of said bulging portion and a supporting member (102) having a plurality of supporting protrusions protruding in a radial direction from the center of the body, arranged equidistantly in a circumferential direction and having a lower elastic modulus than that of said body, and said supporting protrusions are brought into contact with the inner face of said bulging portion. Since the cylinder is an integral type, intrusion of flowing water vapor and vacteria is prevented.

16 Claims, 23 Drawing Sheets

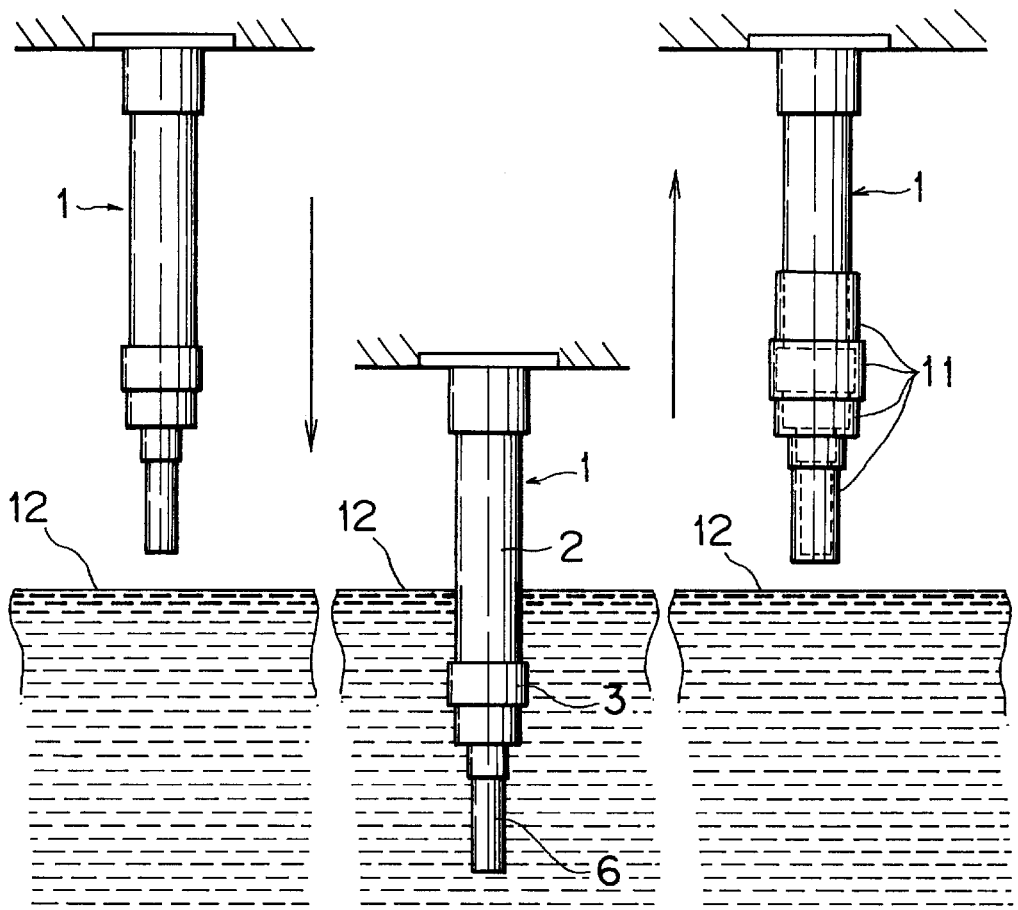

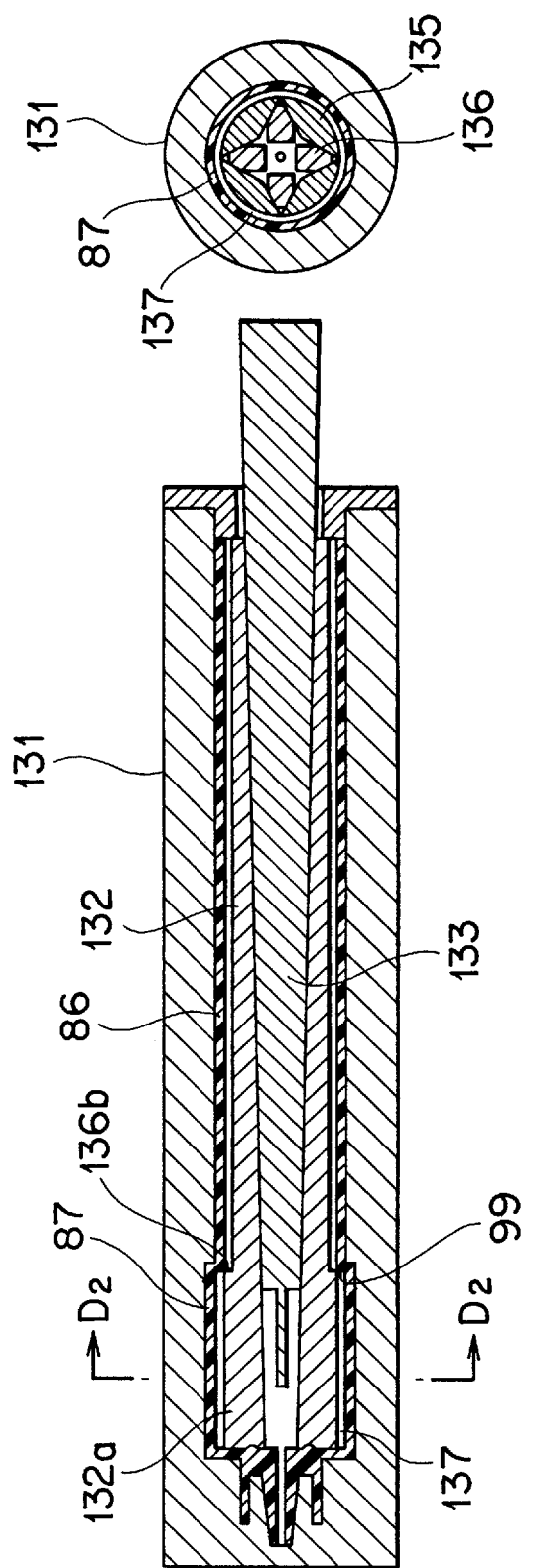

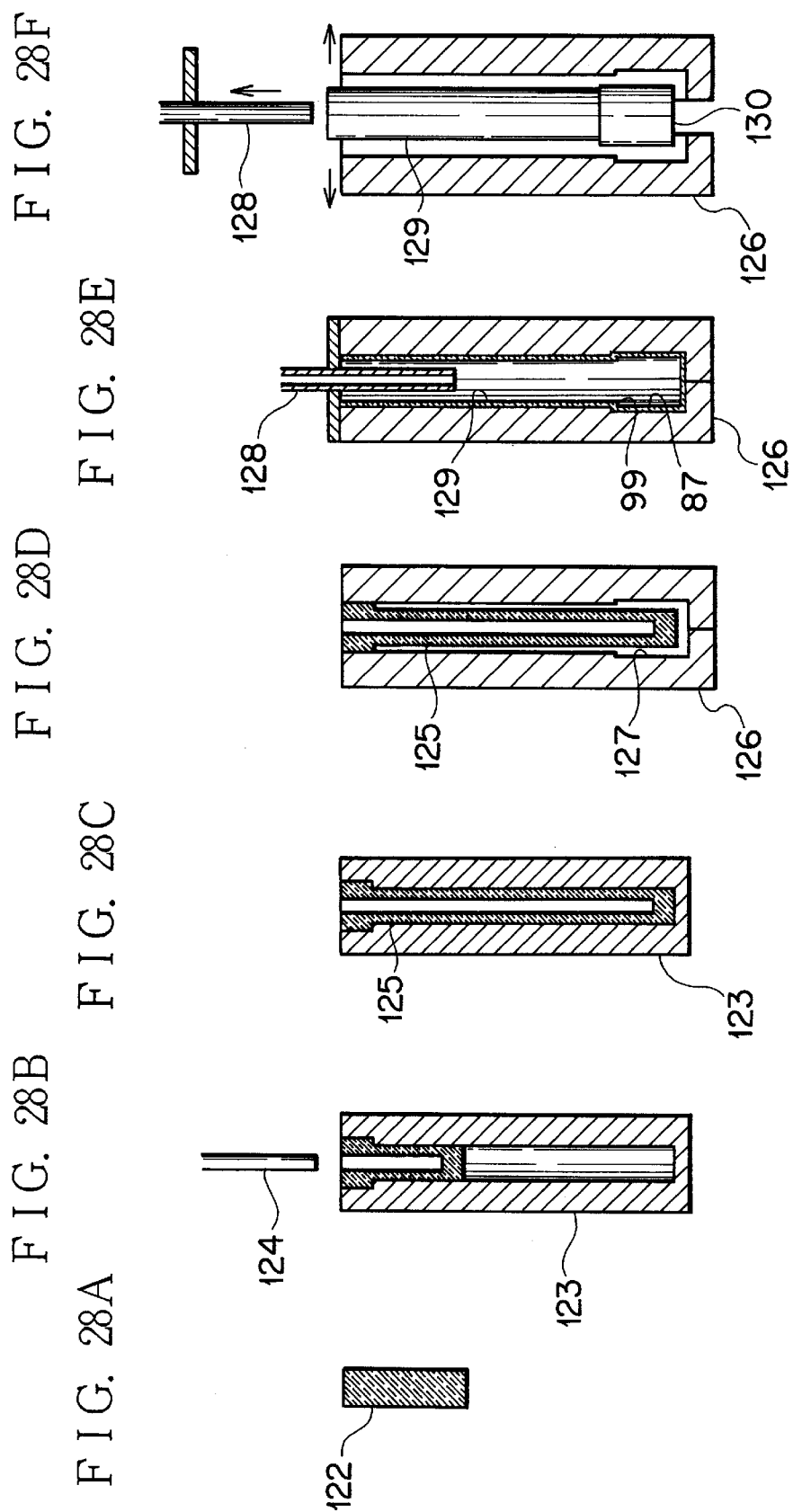

FIG. 30A
FIG. 30B
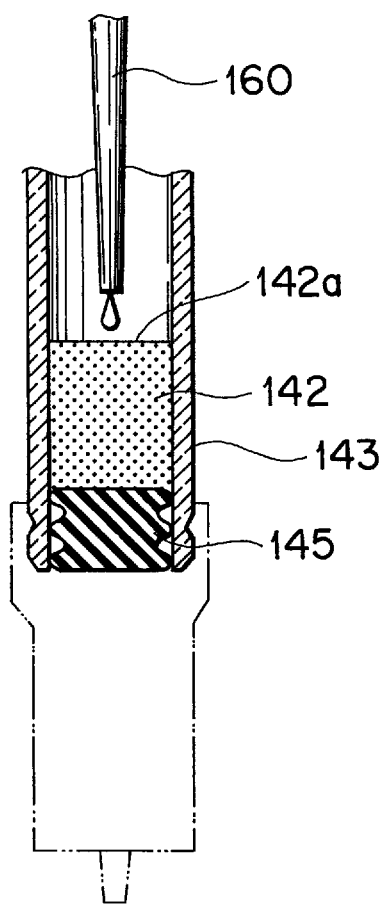
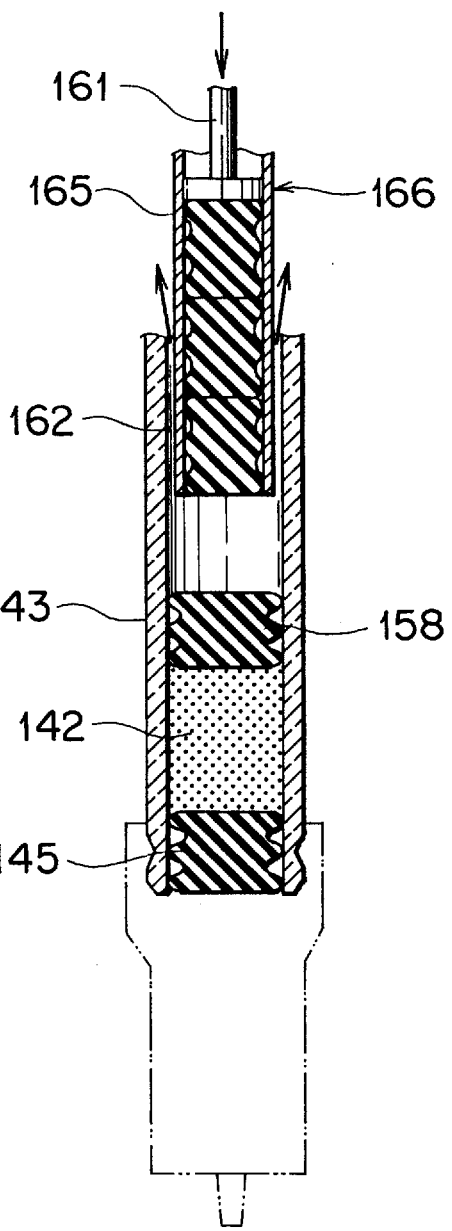

SYRINGE, ITS SEALING STRUCTURE AND SEALING METHOD AND SLIDING VALVE FOR SYRINGE

TECHNICAL FIELD

The present invention relates to a structure and method of sealing a kit-type syringe with a cylinder filled with medicine which has improved sealing property so as to prevent intrusion of flowing water vapor in sterilization and of vacteria in preservation for a long time in a cylinder filled with medicine. The present invention also relates to a sliding valve for a syringe which can be inserted, with no tilt, into the cylinder of a syringe. The present invention further relates to a kit-type syringe having a simple structure which can discharge a medicine liquid through a gap from a sliding valve at a bulging portion of an integral cylinder. These valve and kit-type syringe intend to prevent intrusion of flowing water vapor and vacteria into the syringe.

PRIOR ART

An explanation will be given of the prior art to proposal of the present invention.

In 1969, L. Erberot pointed out a problem of mixing of glass fragment into a medicine liquid. Since then, several serious problems were presented which include coring (phenomenon of cutting rubber pieces) due to piercing of a syringe needle into a rubber stopper for a vial medicine, vacteria pollution in preparation of medicines, etc. In order to obviate these problems, a syringe serving as a vessel, i.e. a medicine kit was developed.

The medicine kit has various merits. For example, the medicine kit, the syringe cylinder of which is filled with a medicine liquid, can prevent mixing of alien substance pollution of vacteria. It can also relax burden of medical workers in preparation of medicine. It is expected to develop increasingly in the future.

The medicine kit used at present can be classified into two structural types.

In the one type, a medicine liquid is put in the conventional cylinder and outside air is shut out by only a cap at a needle connection portion. In the other type, a barrel of plastic is fit in a cylinder body of glass, and a front stopper (or front sliding valve) may shut out the outside air from the medicine liquid.

Generally, laws require that medicines can be preserved for three years. Therefore, the latter type is more preferable than the former type.

Since the inner face of a glass syringe cannot be processed commonly, a syringe composed of a processable barrel of plastic and a cylinder of glass coupled thereto might be an inevitable selection at that time of development.

Recently, the FDA (Food and Drug Administration) in USA required that the kit medicine is sterilized not only before filling of a medicine liquid but also after filling.

However, use of the barrel style syringe gave rise to a problem that flowing water vapor intrudes the barrel in the above post-sterilization.

Thus, the syringe free from intrusion of the flowing water vapor in the post sterilization has become indispensable. In addition, as a premise, it preferable that the syringe has a front stopper as well as a waterproofing cap. Further, the syringe is required to satisfy the following conditions.
1. The barrel and the cylinder body are integral.
2. The structure is simple.
3. The syringe is stable and is easily operable.
4. The production cost is low.
5. The industrial waste is easily processed (i.e. combustible).

A new kit medicine capable of satisfying these conditions has been realized using amorphous polyolefin which has been developed recently. Such a kit medicine has been proposed by the applicant of this application (PCT/JP94/2138).

The details of the above background art will be explained below.

FIG. 29 shows a conventional kit style syringe disclosed in Japanese Patent Publication No. 62-58745.

A syringe 140 permits easy injection by only attachment of a needle in injection, with a cylinder 141 previously filled with a medicine 142. The syringe 140 is composed of a cylinder body 143, a barrel 144 of synthetic resin coupled with the front end thereof, sliding valves 145 (front stopper rubber) and 146 (end stopper rubber or plunger) arranged within the cylinder body 143, a medicine liquid filled between both valves and a cap 148 of synthetic resin mounted so as to cover a syringe needle connection portion 147 at the tip of the barrel 144.

The internal diameter of the barrel 144 is made equal to that of the cylinder body 143. A groove 150 for guiding the medicine liquid is formed on the inner wall of the barrel 144, and is successive to a discharge hole 149 of the needle connection portion 147. In injection, a plunger rod 151 is pushed to shift the sliding valve 145 into the barrel 144 so that the medicine liquid 142 is introduced from the groove into the discharging hole 149.

The cap 148 is secured to a protection cylinder 152 formed on the outside of the needle connection portion 147 of the barrel 144. Specifically, a groove 153 is formed on the inner periphery of the protection cylinder 152. A protrusion 156 of a ring-shaped securing skirt 155 integrally dangling from a flange 154 of the cap 148 is engaged with the groove 153 so that the flange is brought into intimate contact with the protection cylinder 152. The cap 148 serves to prevent dust from intruding into the syringe in preservation.

The syringe 140 described above permits persons engaged in medical treatment to remove the caps 60 and 70, mount a syringe needle and immediately give a patient an injection without labor of filling the medicine liquid. As compared with the conventional syringes, these syringes can prevent inconveniences of pollution of the syringe needle in sucking the medicine liquid, mixing of glass pieces due to ampoule cutting in filling the medicine liquid and mixing of minute fragments of rubber or intrusion of bacteria in thrusting the needle through the rubber stopper of a vial.

However, since the kit medicine serves as a syringe as well as a medicine vessel, the sterilization step is important in its fabrication. Concretely, as recently announced by FDA, in addition to the pre-sterilization before medicine filling, post-sterilization after medicine filling has been required. The pre-sterilization is generally carried out when a medicine manufacturer receives substantially completed syringes (already sterilized) from a medicine manufacturer and remanufactures them. On the other hand, the medicine itself is subjected to the treatment such as auto-cleaving or filter sterilization. The post-sterilization, after medicine filling, is carried out under several conditions, e.g. at 100° C. for 30 minutes and at 121° C. for 20 minutes. The post-sterilization is actually carried out by spraying of flowing steam at 100° C. for 30 minutes or at 120° C. for 20 minutes. For example, where the medicine not heat-resistant like HA (hyaluronic sodium acid) is used as medicine within the syringe), the condition of 100° for 30minutes is set.

However, the syringe 140 described above suffers from the following serious problem that in the post-sterilization, steam or vacteria will intrude into a vacant chamber 157 of the barrel 144 from a small opening between the barrel 144 and the cylinder body 143 or an opening relative to the cap 148 as indicated arrows a and b in FIG. 29. Vacteria are apt to invade from the opening while the syringe is preserved for a long time. The reason is as follows. Since the barrel 144 is attached to the cylinder body 143 by only mechanical fitting, a minute opening occurs inevitably. In addition, since the expansion coefficients of the barrel 144 of synthetic resin and the cylinder body of glass are greatly different from each other, the above opening in heating of the post-sterilization increases. This makes it difficult to hold the mechanical fitting intimate.

On the other hand, in FIG. 29, each of the sliding valves 145 and 158 has two or three annular lips 159 in a horizontal direction on its periphery, and so can smoothly slide with low sliding resistance along the inner surface of cylinder body 143. The sliding valve 158 indicated by a chain line 158 is used to inject two kinds of medicine liquids separately by a single pushing operation. The front and intermediate sliding valves 145 and 158 have the same shape.

The sliding valves 145 and 158 are inserted within the cylinder body 143 by a manner shown in FIGS. 30A and 30B. First, as shown in FIG. 30A, the front sliding valve 145 is inserted in the front end of the cylinder body 143. The front sliding valve 145 can be manually inserted from the front end of the cylinder body 143 or inserted using a plugging jig 166 shown in FIG. 30B.

After the front sliding valve 145 is inserted, a medicine liquid is injected from a nozzle 160 into the cylinder body 143. Next, as shown in FIG. 30B, the intermediate sliding valve 158 (in the case of a two-layer type) or the rear sliding valve 146 (in the case of a single layer type) is inserted flush with a liquid surface 142a.

Specifically, the sliding valves 145 and 168 are previously confined with their diameters shrunken within a metallic cylindrical tube 165. A push rod 161 is pushed to push the sliding valve 158 into the cylinder body 143 in a spidwad gun manner. The air between the medicine liquid 142 and the sliding valve 158 is vented externally from an opening 162 between the cylindrical tube 165 and the cylinder body 143 as indicated by arrows. When the intermediate sliding valve 158 is inserted, the second medicine liquid is injected in a vacuumed state to prevent air from being mixing into the second medicine liquid. This is because where air is mixed in the second medicine liquid, the one-shot operation of the plunger rod 151 may inject air into a human body together with the second medicine liquid or vacteria in the air may mix into the medicine liquid during preservation.

However, the sliding valves 145 and 158 of the conventional syringe have the following disadvantages. As shown in FIG. 31, when the front sliding valve 145 is inserted in the cylinder body 143 manually or using the plugging jig 166, it is apt to be held inclined (i.e. the axial line of the cylinder body 143 is not coincident to that of the sliding valve 145). In this case, the liquid face 142a rises by the volume corresponding to inclination of the sliding valve 145. For this reason, when the intermediate or the rear sliding valve 158 or 146 is plugged, the medicine liquid bulges out and is stuck onto the outer peripheral surface. This produces a white stain-like pattern 163, thus making a poor appearance of the syringe. Inversely, inclination of the sliding valve 145 increases the internal volume of the cylinder so that air may be mixed into the cylinder. Even if the front sliding valve 145 is located at a correct position, if the intermediate or rear sliding valve 158 or 146 is inserted inclinedly, these problems occur similarly.

One cause of inclination of the sliding valve 158 is that when the sliding valve 158 is plugged out from the cylindrical tube 165, the entire circumference of the circular lip 159 rarely leaves simultaneously from the front end of the cylindrical tube 165. Specifically, since circular lip 159 is apt to warp in an axial direction (front-and-rear direction), a part of the entire circumference is deformed to be twisted, thus making the degree of warping in the entire circumference not uniform. Thus, the sliding valve 145 or 158 is apt to incline in manual insertion or plugging.

On the other hand, vacuum evacuation is made to prevent air from entering circumferential grooves 164 between the annular lips 159 of the intermediate sliding valve 158 in plugging. In the case of incomplete vacuum evacuation, air is apt to enter the circumferential grooves 164. In order to obviate such an inconvenience, in the application of PCT/JP/2138, the applicant proposed a structure in which the annular lips 159 are provided with grooves for venting to fill the circumferential grooves with the medicine liquid 142.

In view of the above circumstance, the present invention intends to provide a sealing structure or sealing method of a syringe in which in a post-sterilization step, water vapor does not intrude into the inside of a syringe (the inside of a vacant chamber) from an opening of a barrel or cap and vacteria do not intrude in preservation for a long time. The present invention also intends to provide a sliding valve for the syringe which can be inserted horizontally with no inclination in a cylinder in insertion to prevent stain from being created due to bulging-out of a medicine liquid and to intrusion of vacteria due to air mixing into the cylinder. The present invention further intends to provide a kit-style syringe having a simple structure which can prevent intrusion of water vapor in a post-sterilization step and intrusion of vacteria in preservation for a long time.

DISCLOSURE OF THE INVENTION

In order to attain the above object, as a sealing structure and a sealing method of a syringe, in a syringe in which a barrel having a syringe needle connection portion is fit in a cylinder body and a cap covering the syringe needle connection portion is fit in the tip of the barrels, the present invention adopts the first structure wherein a waterproofing film is continuously adhered onto the surfaces of the cap, barrel and cylinder to cover the fitting areas between the cap and the barrel and between the barrel and the cylinder body whereby intrusion of flowing water vapor in post sterilization and of vacteria in preservation for a long period is prevented, and in a syringe in which a cap covering a syringe needle connection portion is fit in the tip of a cylinder, the second structure wherein a waterproofing film is continuously adhered onto the surfaces of the cap and cylinder to cover the fitting areas between the cap and the cylinder whereby intrusion of flowing water vapor in post-sterilization and in preservation for a long time is prevented.

Said film is required to be made of synthetic resin having a higher melting point than the temperature in a post-sterilization of the syringe.

The present invention adopts the first method of sealing a syringe comprising the steps of immersing the syringe in the syringe in molten or solved synthetic resin and lifting it to adhere a film of synthetic resin onto the surface of the syringe inclusive of a fitting area between a barrel having a syringe needle connection portion and a syringe body and/or between the barrel and a cap covering the syringe needle connection portion, whereby intrusion of flowing water vapor in post sterilization and of vacteria in preservation for a long period, and adopts the second method of sealing a syringe comprising the step of applying a sealing material on a fitting area between a barrel having a syringe needle connection portion and a syringe body and/or between the barrel and a cap covering the syringe needle connection portion, and combining the barrel and the cap, whereby intrusion of flowing water vapor in post sterilization and of vacteria in preservation for a long period.

As a sliding valve for a syringe, the present invention adopts a first sliding valve, wherein a wavy inclined lip is continuously protruded from the outer surface of an elastic short cylindrical body in its circumferential direction. An annular lip is formed at the one end of the cylindrical body. The annular lip has a recess for introducing a medicine liquid.

The present invention adopts the second sliding valve for a syringe wherein an annular lip is protruded from the outer surface of a short cylindrical body at its end, and plural pairs of inclined lips each pair having an invented ᴧ shape closing toward its other end thereof are protruded therefrom.

The inclined lips may be arranged in plural stages. In the first sliding valve, preferably, said wavy inclined lips are arranged in plural stages, and the other inclined lips than one inclined lip each has a recess for introducing medicine liquid.

The present invention adopts the third sliding valve wherein an annular lip is protruded at one end of a short cylindrical body and plural strips of wavy inclined lips are provided in an axial direction on the outer surface of the body.

The present invention adopts the fourth sliding valve for a syringe wherein plural inclined lips which cross in a shape of a sea slug wall are protruded from the outer surface of a short cylindrical body.

As a syringe according to the present invention, the present invention adopts the basic structure of a syringe wherein at the tip of a cylinder, a bulging portion having a larger inner diameter than that of the cylinder is formed integrally to the cylinder and the inner diameter of said bulging portion is larger than the outer diameter of an elastic sliding valve slidable in said cylinder in its free state so that a medicine liquid behind said sliding valve is discharged through a gap between said bulging portion and said sliding valve into a syringe needle connection portion. The cylinder may be made of glass or synthetic resin such as amorphous polyolefin.

A syringe structure is preferable in which on the bottom wall of said bulging portion successive to said syringe needle connection portion, a protrusion for supporting said sliding valve is formed so that a gap for discharging a medicine liquid is formed between said protrusion and said sliding valve. Another syringe structure is also preferred in which on an end wall of said sliding valve opposite to the bottom wall of said bulging portion, a medicine discharging groove is formed to communicate with an inner hole of said syringe needle connection portion. Said sliding valve includes a body having a smaller diameter than the inner diameter of said bulging portion in a free state and a supporting member having a plurality of supporting protrusions protruding in a radial direction from the center of the body, arranged equidistantly in a circumferential direction and having lower elastic modulus than that of said body, and in a free state of the sliding valve, said supporting protrusions are brought into contact with the inner face of said bulging portion to support the sliding valve stably. Said supporting member includes a center portion located at the center of the body and a plurality of elastic portions extending radially from the center, and each of said elastic portions has said supporting protrusion at its end.

The sealing structure for said syringe may be applied to the syringe according to the present invention.

BRIEF DESCRIPTION OF THE DRAWINGS

FIG. 2 shows an example of a method of sealing a syringe; (a) is a side view of the state where a syringe has been transported above a resin liquid, (b) is a side view of the state where the syringe is immersed in the resin liquid, and (c) is a side view where the syringe has been lifted from the resin liquid.

FIG. 26(a) and FIG. 27(a) are longitudinal sectional views showing a method for molding a cylinder with synthetic resin material.

FIG. 27(b) is a sectional view taken in line $D_2$—$D_2$ of FIG. 27(a).

FIG. 28(a) to FIG. 28(f) are longitudinal sectional views for showing a method for molding a cylinder of glass material.

FIGS. 30(a) and 30(b) are longitudinal sectional views showing a method of plugging a sliding valve toward a cylinder.

BEST MODE FOR EMBODYING THE INVENTION

Embodiment 1

Figure 1A:
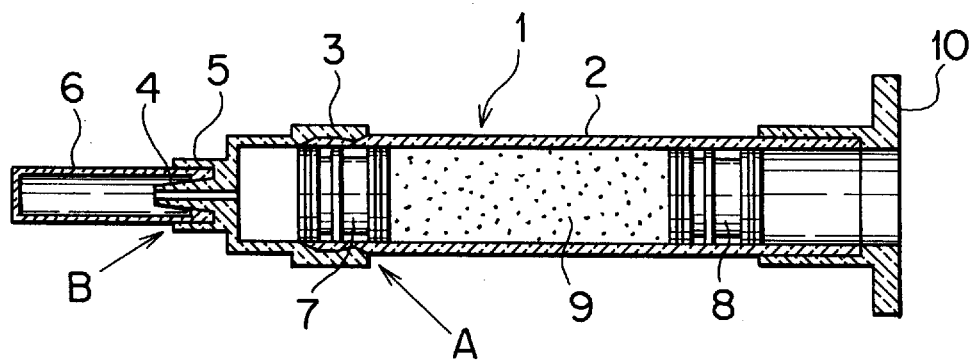
FIG. 1 shows an example of a sealing structure of the syringe according to the present invention; (a) is a longitudinal sectional view showing the syringe before seal-peel treatment, and (b) is a longitudinal sectional view of the syringe after subjected to the seal peel treatment.

The sealing structure or sealing method of a syringe according to the present invention mainly adopts a "seal peel" treatment, which is generally used for prevention of rust in the field of general industry in order to cover the area extending from a cap at a tip of a syringe to a cylinder body through an intermediate barrel with a thin film of synthetic resin, thereby preventing flowing water vapor from intrusion of a kit medicine in post-sterilization. The "seal peel", i.e., a film which is thin enough to peel off by a finger is mainly made of thermoplastic resin and must withstand the temperature at post-sterilization. Where the temperature of post-sterilization is low (not higher than 100° C.), a film material such as paraffin other than the synthetic resin is used can be used.

The seal peel treatment is performed by techniques of dipping an object into melting (dissolving) resin or application thereof. In the dipping technique, the thermoplastic resin can be molten by heating, melting by solvent, etc. The kind of resin can be selected in accordance with the medicine liquid filled in a syringe. In dipping, the resin must be heated and molten in a temperature range where the effect of the medicine is not reduced, and the syringe must be subjected to post-sterilization in the temperature range. Where the syringe is structured as an integral cylinder of resin (as proposed in FIG. 16 of PCT/JP94/2138 by the applicant of this application) or the conventional cylinder of glass, the area inclusive of the cap at the tip and the cylinder body can be subjected to the seal peel treatment to prevent intrusion of flowing water vapor from the cap fitting portion.

Instead of the above seal peel treatment, the fitting portion between the barrel or cap and the cylinder body of a syringe may be covered with a sealing member such as a silicon sealant, and thereafter the barrel or cap may be attached to the cylinder to fill the gap between the fitting portions with the sealing member.

In the description of this specification, the term "dissolve" is defined to include both "solve" and "melt".

Now referring to the drawings, a detailed explanation will be given of embodiments of the sealing structure and method of the syringe according to the present invention.

FIG. 1(a) shows a kit-style syringe 1 like the prior art before the seal peel treatment. Intrusion portions of flowing water vapor indicated by arrows a and b are located between a cylinder body 2 of glass and a barrel 3 of synthetic resin and between a protection cylinder 5 outside the a needle connection portion 4 at a barrel tip and a cap 6 of synthetic resin. The cap 6 may have the same fitting structure as that of the prior art shown in FIG. 23, or otherwise may be simply fit between the needle connection portion 4 and the protection cylinder 5. Within the cylinder 2, sliding valves 7 (front stopper rubber) and 8 (end stopper rubber) are inserted and between both valves 7 and 8, a medicine liquid 9 is filled. A flange member 10 is fit over the rear of the cylinder body 2. A plunger rod (not shown) is screwed into the sliding valve (end stopper rubber) 8.

Figure 1B:
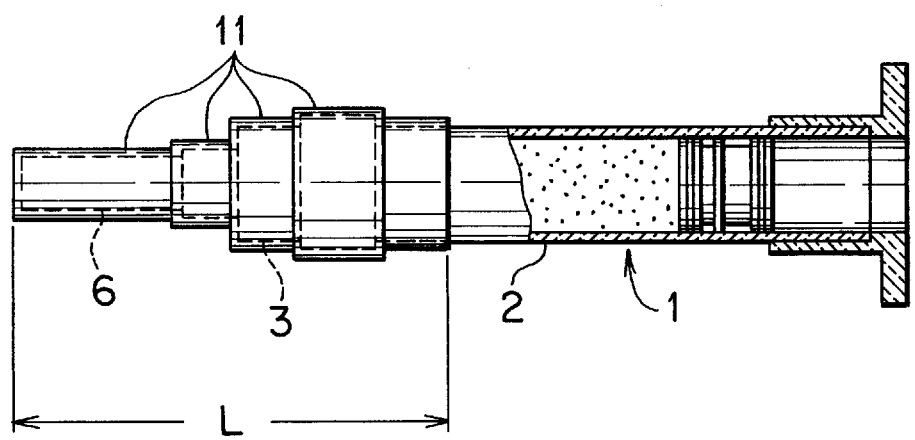

FIG. 1(b) shows the state of the syringe 1 subjected to the seal peel treatment. As seen from FIG. 1(b), in an area L extending from the tip of the cap 6 to a mid-point of the cylinder body 2 (near the tip) via the barrel 3, their surfaces are continuously covered with a thin film (seal peel) 11 made of synthetic resin (thermoplastic resin). The seal peel 11 is kept in intimate contact with the above surfaces of the cap 6, barrel 3 and cylinder body 2 to cover the intrusion position of the flowing water vapor indicated by arrows a and b so that these positions are completely shut off from the outside. For example, the seal peel has a thickness of 0.2–0.3 mm. In using the syringe, simultaneously when the cap 6 is taken off, the seal peel can be broken easily.

The seal peel 11 of resin must have the following properties.

(1) It is not dissolved under the condition of the temperature (normally 100° C. or higher) of flowing water vapor and a working time (normally 3–30 minutes) in a post-sterilization step.

(2) It can satisfy the condition of the above item (1) and also has a sufficiently low melting point (adopted in only the melting technique described later).

(3) It contains no poison (i.e. is applicable to medicine, food vessel, etc)

(4) The seal peak having a suitable thickness formed in hardening can be peeled by a nail, for example. Thus, it can be easily peeled from an object to be covered (cap 6, barrel 3 and cylinder body 2). The film material satisfying these conditions includes polyethylene, vinyl chloride, polyvinyl acetate and polyvinyl acetal, etc.

FIG. 2(a) to (c) show an example of the method of providing a sealing structure of the syringe described above.

First, as shown in FIG. 2(a), the syringe 1 is transported to above thermoplastic resin 12 molten, and arranged vertically as shown in FIG. 2(a). As shown in FIG. 2(b), the front half (cap 6, barrel 3 and the front end of the cylinder body 2) of the syringe 1 is immersed in a liquid of the resin 12. As shown in FIG. 2(c), the syringe 1 is drawn up from the resin liquid 12 thereby drying (hardening) the surface of the syringe 1 to which the resin has been applied. Thus, the hardened seal peel 11 is formed on the surface of the syringe 1 inclusive of the intrusion positions of flowing water vapor.

The thermoplastic resin can be molten in a resin bath (not shown) by the following two techniques.

The first technique is to heat the thermoplastic material to a melting point in FIG. 2(a) (melting technique). In this case, after the syringe 1 is drawn up from the molten resin 12, it is cooled to obtain the hardened seal peel 11. The resin material may be e.g. polyethylene (having large molecular weight) and vinyl chloride. Incidentally, polyethylene and vinyl chloride (hard), which have melting points of 120° C. or higher and 127° C., respectively (see "PLASTIC HANDBOOK" BY KOGYO CHOSAKAI), can sufficiently endure the post-sterilization of 100°–121° C. The melting technique has a typical condition of a working temperature of 110°–120° C., a syringe immersing time of 1 sec or shorter and a cooling time after drawing-up of 0.5–1 minutes.

The second method is to solve the synthetic resin by solvent. In this case, after the syringe 1 is drawn up from the resin liquid 12 containing solvent, and it is dried by wind to remove the solvent, thereby providing the hardened seal peel. The solvent may be also organic solvent such as acetone. This technique has a condition of a temperature of the liquid of a room temperature (heating or cooling is not carried out.), an immersing time of the syringe of 1 sec or shorter and a drying time of 0.5–1 hour. The drying time, because the solvent is removed by evaporation, is longer than the cooling time in the melting technique.

The above working condition and property of the resin are only an example. Since the working condition (temperature and time) of the post-sterilization is changed in accordance with the medicine 9 within the syringe 1, the optimum kind and property of the resin to be used for the seal peel should be selected in each case.

Even with a difference in the thermal expansion coefficient between the cylinder body 2 of glass and the barrel 3 of synthetic resin, the above sealing structure and technique has the following operational effects.

(1) In hardening (or drying), the resin material forms the seal peel 11 while it is shrunken in hardening (or drying). For this reason, even when the syringe is heated in the post-sterilization step and the barrel is expanded, the peel seal holds the intimate contact with the object.

(2) Since the seal peel 11 is formed not only on the areas where openings are formed but also on the wide range extending over these areas, even if the contact degree is lowered, no flowing vapor intrudes into the cylinder body.

(3) The water contents of plastic, which is generally as low as 0.01% or less (thickness of 3 mm and 24 hours), is not entirely problematic in the working time (30 minutes in maximum) for sterilization. There is no fear of intrusion of the flowing water vapor through the seal peel 11.

(4) The seal peel 11 can prevent not only intrusion of the flowing water vapor but also vacteria in post-sterilization and in preservation for a long time.

As described above, in accordance with the first embodiment (claim 1 to 4) of the present invention, since the seal peel for water proofing covers the fitting portion between the barrel and cylinder body and the fitting portion relative to the cap, the intrusion of the flowing water vapor into the syringe in the post-sterilization can be surely prevented. In addition, intrusion of vacteria preservation for a long time is prevented. Further, in accordance with claim 5, the fitting portions relative the barrel and cap are sealed by the sealing member so that the intrusion of the water flowing vapor into the syringe can be prevented.

Embodiment 2

The sliding valve of a syringe according to the present invention is mainly made of elastic material such as synthetic rubber and has wavy inclined lips protruded discontinuously or continuously protruded from the outer surface of a short cylindrical body. The wave shape may be defined as a zigzag, a sinusoidal wave or a wave with the upper and lower ends sharpened or rounded. Where the inclined lips are formed discontinuously, a recess for introduction of a medicine introduction, opening or gap will be formed therebetween. In order to obviate such an inconvenience, at the one end of the body, a continuous lip such as a ring-shaped lip or other wavy lip is formed. The continuous and discontinuous inclined lips may be provided in a multi-step.

Referring to the drawings, a detailed explanation will be given of various examples of the sliding valve for a syringe according to the present invention.

Figure 3:
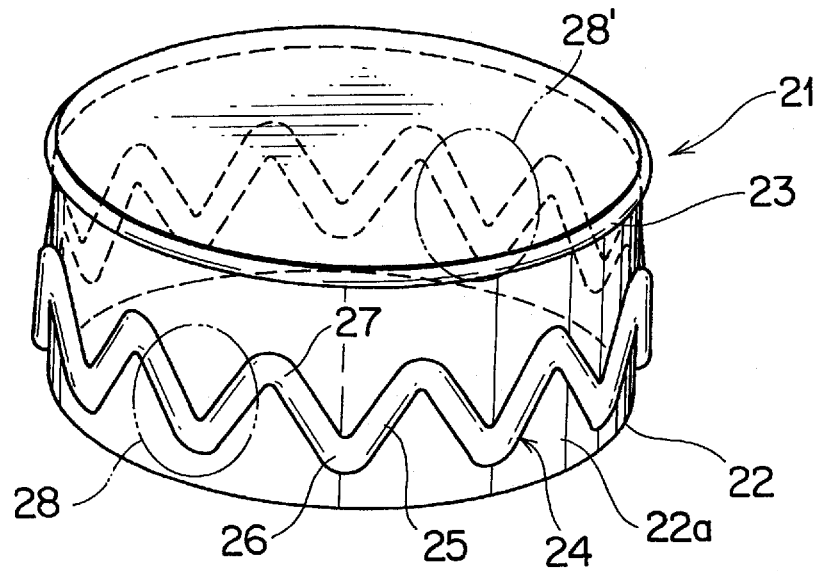
FIG. 3 is a perspective view of a first example of a sliding valve for a syringe according to the present invention.
Figure 4:
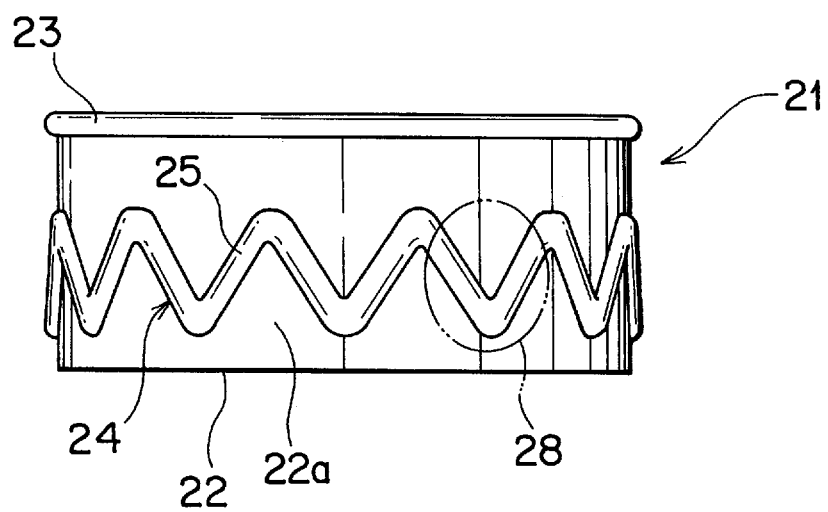
FIG. 4 is a side view of the above first example.

FIG. 3 to 4 show a first example of the sliding valve for a syringe according to the present invention. The sliding valve 21 is composed of a short cylindrical elastic body 22, a single-strip annular lip 23 protruded from the circumference of the one end (upper end) of the body 22, and a wavy lip (wavy inclined lip) 24 continuously protruded in a wave-shape on the outer surface of the body 22. The annular lip 23 has the same shape as that of the prior art and located near the rear piston of a syringe as seen from FIG. 13. The wavy lip 24 is continuous in a circumferential direction of the body 22, and is composed of plural linear slopes (sloped lips) 25 inclined by an acute angle for an axial line of the body 22 and upper and lower bends 26 and 27 connecting the sloped lips 25 to form V-shapes to each other. The protrusion of the wavy lip 24 is flush with the annular lip 23.

In this example, the wavy lip 24 is composed of ten V-shapes which are successively formed over the entire circumference of the body 22. At a point opposite to a certain V-shape 28, another V-shape having the same shape is located. Where even number of V-shapes 28 are formed, in inserting the sliding valve, the sliding resistance of one V-shape 28 to the inner face of the cylinder is equal to that of another V-shape at the opposite position out of phase of 180°. Thus, the sliding valve is more difficult to incline.

An odd number of V-shapes may be formed. In this case also, the warp of each of the V-shapes 28 uniformly occurs over the entire circumference of the sliding valve 21 to make the resistance uniform. In addition, the edge effect of the V-shape 28 stabilizes and improves capabilities of insertion and linear advancement for the cylinder. This effect exerted on the entire circumference of the sliding valve 21 in addition to the above uniform warp of the V-shapes 28 can prevent the sliding valve 21 from being inclined. Although the wavy lip 24 is composed of the straight sloped lips 25, it may be a sinusoidal wavy lip defined by e.g. $y=\sin\theta$ to obtain the same advantage.

Figure 5:
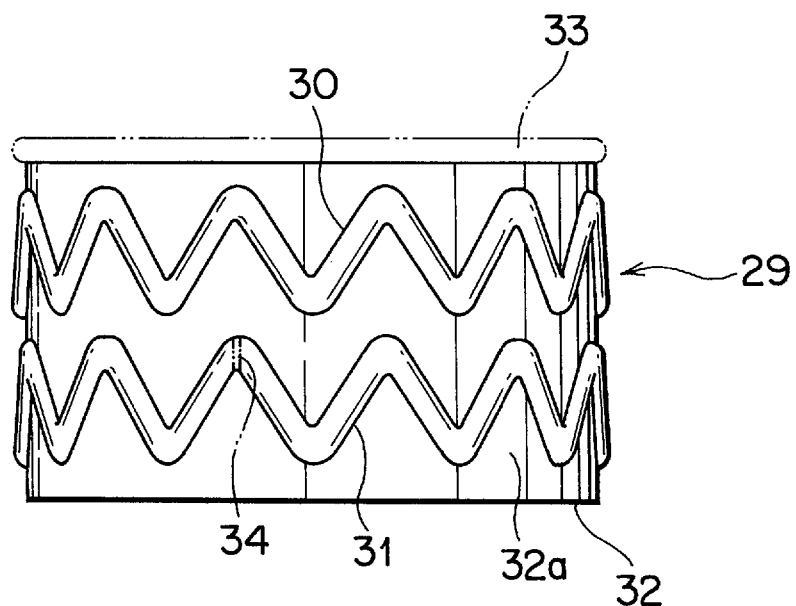
FIG. 5 is a side view of a second example of the sliding valve for a syringe according to the present invention.

FIG. 5 shows the second example of the sliding valve for a syringe.

The sliding valve according to this example includes wavy lips (wavy sloped lips) 30 and 31 each having the same shape as that of the wavy lip in the first embodiment and arranged in parallel vertically on the outer surface of a short cylindrical body 32. The entire length of the body 32 is longer than that of the body 22 in the first embodiment. The wavy lips 30 and 31 have sufficient continuous sealing property in the circumferential direction so that provision of an annular lip 33 indicated by a dotted line at the one end of the body 32 is not necessarily required. With no annular lip 33, the one wavy lip 31 provided with a recess 34 may be used for an intermediate sliding valve. Provision of the two wavy lips 30 and 31 in parallel in this example improves difficulty of inclination and capability of linear advancement of the sliding valve for the inner wall of the cylinder.

Figure 6:
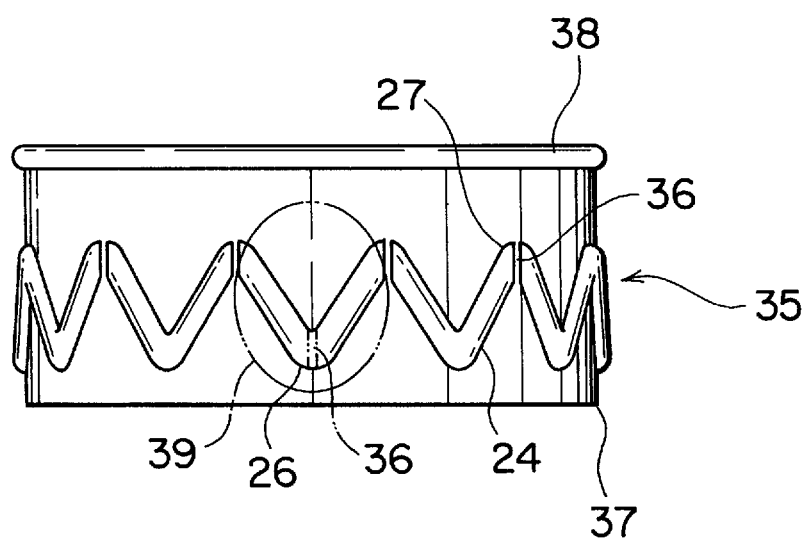
FIG. 6 is a side view of a third example of the sliding valve for a syringe according to the present invention.

FIG. 6 shows the third example of the sliding valve for a syringe. A sliding valve 35 in this example is used as an intermediate sliding valve. In this example, recesses (or grooves) 36 in an axial direction are provided at the upper bends 27 of the wavy lip (wavy sloped lip) 24 in the first example shown in FIG. 4 so that a medicine liquid can be introduced from the lower end of a body 37 in between an annular lip 38 at the upper end of the body 37 thereby to prevent air stagnancy between the lips 24 and 38. The wavy lip 24 is divided into plural V-shapes 39 by the recesses 36. The recesses 36 may be formed at the lower bends 26 but not at the upper bends 27 as indicated by dotted line; or otherwise at both bends 26 and 27.

Figure 7:
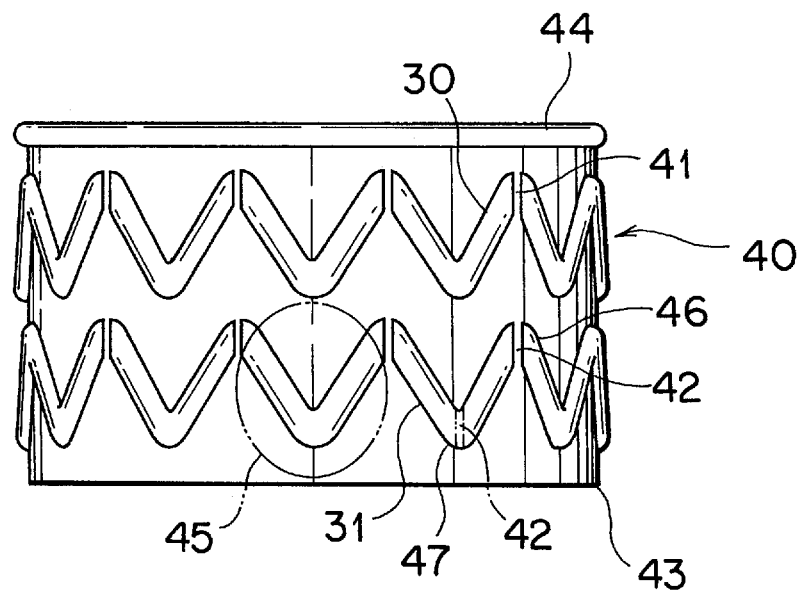
FIG. 7 is a side view of a forth example of the sliding valve for a syringe according to the present invention.

FIG. 7 shows the fourth example of the sliding valve for a syringe.

A sliding valve 40 in this embodiment is also used as an intermediate sliding valve.

Figure 13:
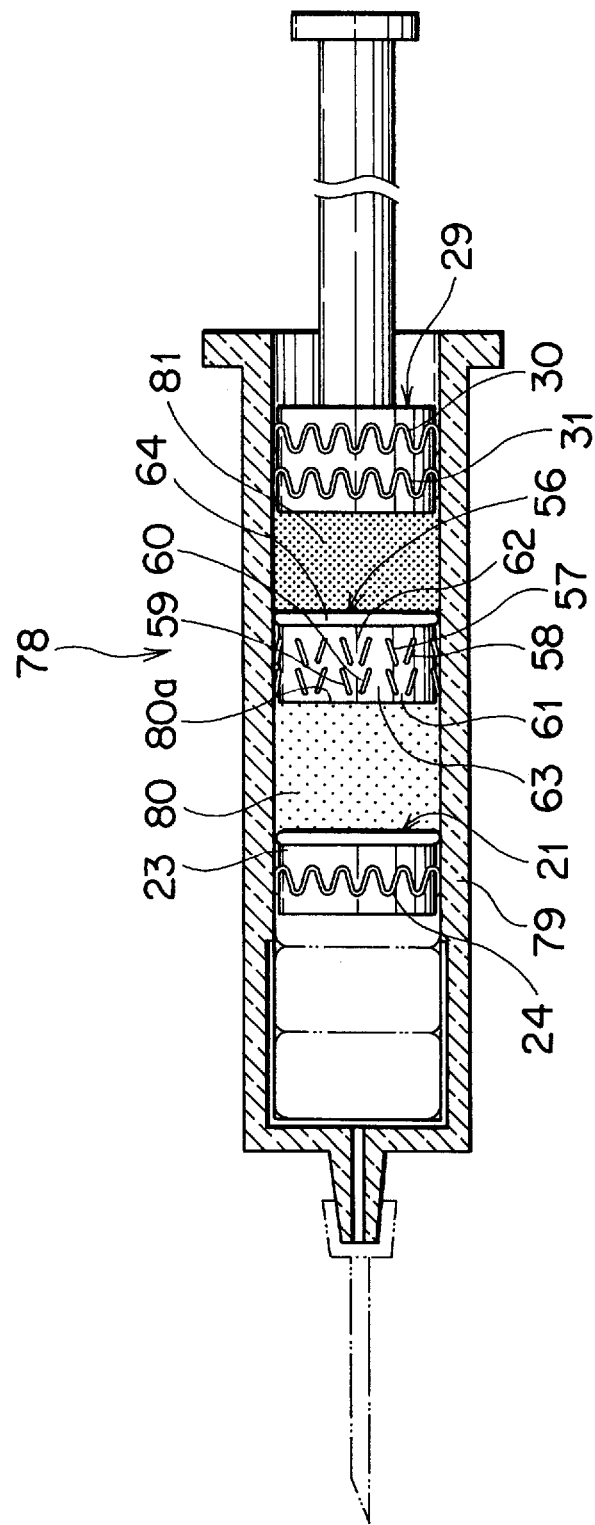
FIG. 13 is a longitudinal sectional view showing one example of a kit-style syringe incorporating a sliding valve for a syringe.

In this example, recesses (or grooves) 41 and 42 in an axial direction are provided at upper and lower wavy lips (wavy sloped lip) 30 and 31 in the second example shown in FIG. 5, respectively. An annular lip 44 is formed at the upper end of a short cylindrical body 43. Thus, a medicine liquid can be introduced in between the upper and lower wavy lips 30 and 31 and in between the upper wavy lip 30 and the annular lip 44. The annular lip 44 is located near the rear piston as shown in FIG. 13. As in the third example of FIG. 6, the wavy lips 30 and 31 are divided into plural V-shapes 45 by the recesses 41 and 42, respectively. The recesses 41, 42 may be formed at the lower bends 47 but not at the upper bends 46 as indicated by dotted line.

The second example of FIG. 5 to the fourth example of FIG. 7 can provide the same operation and effect as those of the first example of FIG. 1. The third example of FIG. 6 and the fourth example of FIG. 7 may be used as a front sliding valve or rear sliding valve in FIG. 13.

Figure 8:
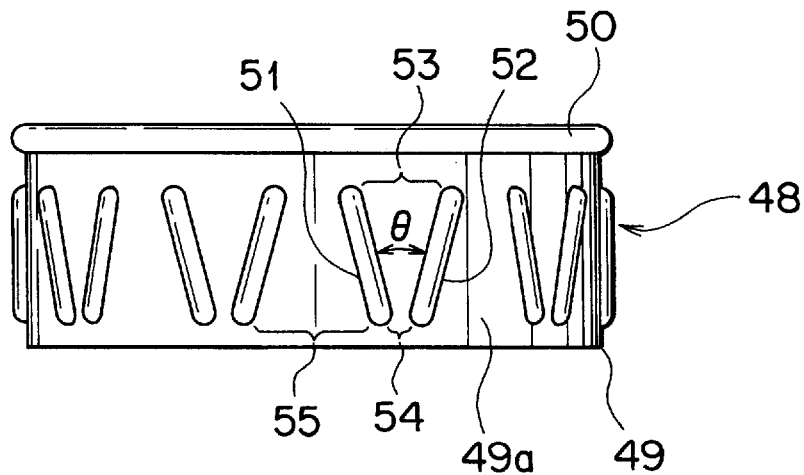
FIG. 8 is a side view of a fifth example of the sliding valve for a syringe according to the present invention.

FIG. 8 shows the fifth example of the sliding valve for a syringe.

A sliding valve 48 in this embodiment is similar to the sliding valve 35 according to the third embodiment of FIG. 5 when the recesses 36 are formed at the upper and lower bends 26 and 27. Specifically, an annular lip 50 is formed at the upper end of a short cylindrical body 49, and plural pairs of sloped lips 51 and 52 each pair having a substantially-inverted ⋀ shape (which is a V-shape with a lower end cut) are formed on the outer surface of the body 49.

The sloped lips 51 and 52 protrude from the outer surface of the cylindrical body 49 in the shape of a sea slug, and arranged linearly in an acute angle from an axial line of the cylindrical body 49. A pair of sloped lips 51 and 52 constitute a wide open area 53 at the upper end, and a narrow opening area 54. An even number of pairs of sloped lips 51 and 52 are arranged at equidistantly or regular intervals, and a tapered wide gap 55 is open between the adjacent pairs of sloped lips.

From the respective opening areas 53 and 54 and the gap 55, a medicine liquid is introduced from the annular lip 50. The opening angle θ formed by the pair of lips 51 and 52 constituting a substantial V-shape is preferably 30° or less taking capabilities of insertion and linear advancement into consideration. But the opening angle exceeding 30° leads to no problem in an actual use.

Figure 9:
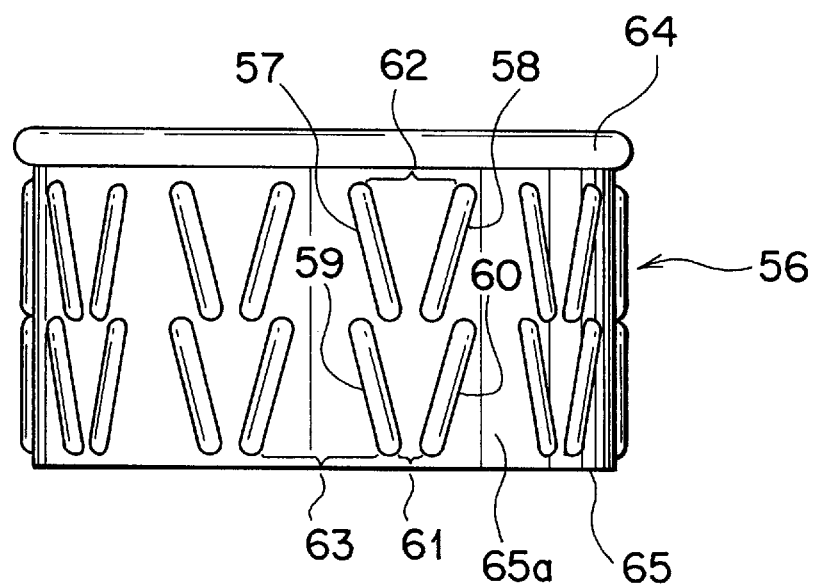
FIG. 9 is a side view of a sixth example of the sliding valve for a syringe according to the present invention.
Figure 10:
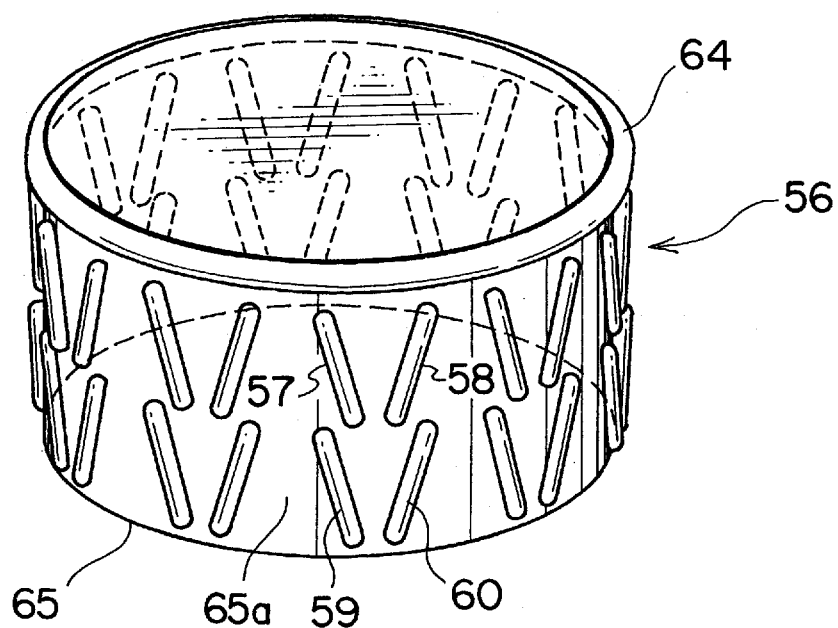
FIG. 10 is a perspective view of the above six example.

FIGS. 9 and 10 shows the sixth example of the sliding valve for a syringe.

A sliding valve 56 according to this example includes plural pairs of upper and lower sloped lips 57, 58 and 59, 60 each pair having the same sea-slug shape as those of the sloped lips 51, 52 in the fifth example of FIG. 8 and arranged in parallel vertically on the outer surface of a relatively lengthy short cylindrical body 32. The center lines of the upper and lower pair of sloped lips 57, 58 and 59, 60 are coincident to each other. In the sliding valve 56 according to this example, a medicine liquid is guided from the openings 61, 62 between the sloped lips 57, 58 and 59, 60 and the gap 63 towards the annular lip 64.

In the fifth and sixth examples of FIGS. 8 to 10 also, pairs of substantial V-shaped sloped lips 57, 58 and 59, 60 have sliding areas for the inner wall of the sliding valve 21 or 56 over its substantial entire length, like the V-shape 28 in the first embodiment of FIG. 3. For this reason, the rigidity of the sliding face of the sliding valve 56 which is an elastic member can be improved so that the deformation of the entire circumference can be made uniform as compared with the conventional sliding valve provided with only the annular lip. The edge effect of the substantial V-shape stabilizes capabilities of insertion and linear advancement to prevent the sliding valve from inclining. The sliding valve 56 is mainly used as an intermediate sliding valve.

Figure 11:
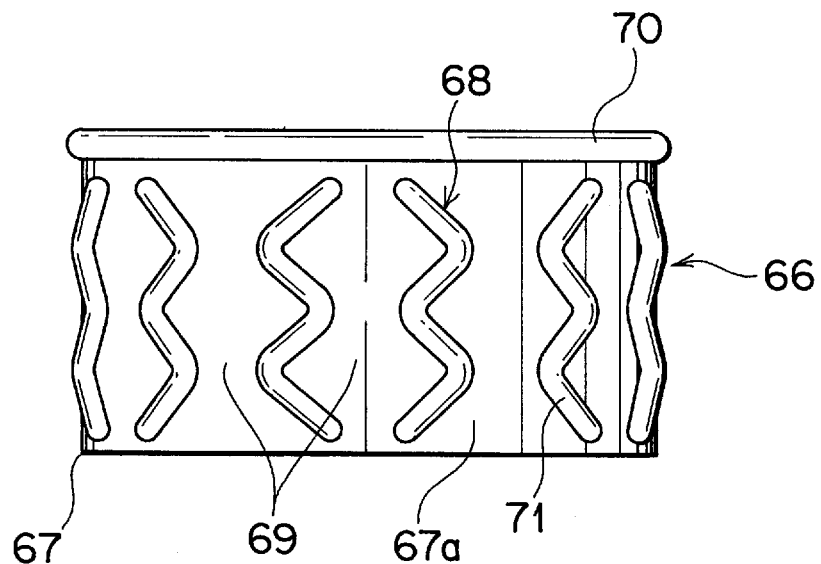
FIG. 11 is a side view of a seventh embodiment of the sliding valve for a syringe according to the present invention.

FIG. 11 shows the seventh example of the sliding valve for a syringe.

A sliding valve 66 includes plural wavy lips (wavy sloped lips) 68 in the first embodiment of FIG. 1 arranged in an axial direction on an outer surface 67a of a lengthy body 67. In this example, although plural pairs of the wavy lips 68 are arranged oppositely in a symmetrical shape, respectively, the respective wavy lips may be aligned in the same form. Between the adjacent wavy lips 68, one of gaps 69 is formed. From the gap 69, a medicine liquid is guided toward an annular lip 70. Each wavy lip 68 is composed of plural sloped lips 71 continuous in zigzag which can provide the same functional advantage as in the above examples.

Figure 12:
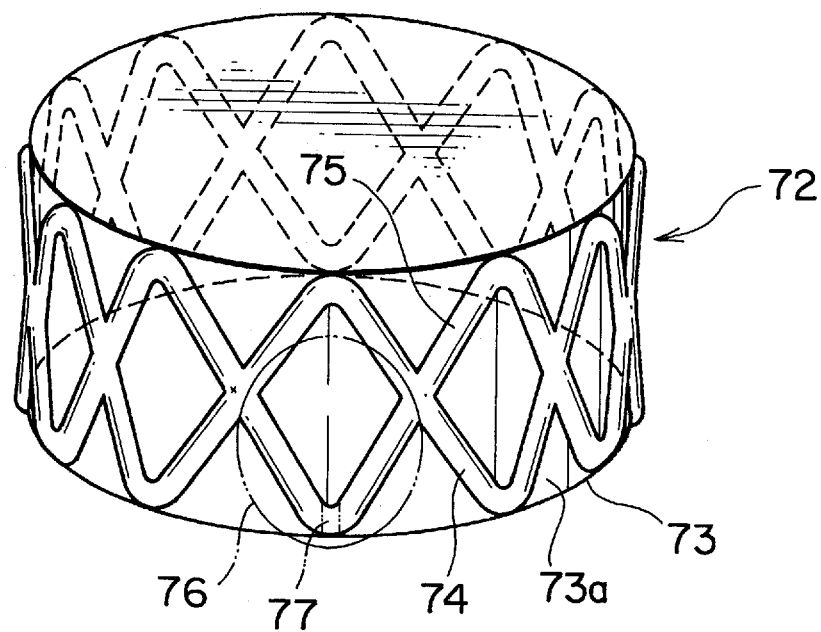
FIG. 12 is a side view of an eighth example of the sliding valve for a syringe according to the present invention.

FIG. 12 shows the eighth embodiment of the sliding valve for a syringe.

A sliding valve 72 in this embodiment is a basic form of all the sliding valves hitherto described. The sliding valve 72 includes plural sloped lips 74 and 75 crossing in a "sea slug wall" shape which are continuously protruded from the outer surface of a short cylindrical body 73. In this example, although two strips of continuous sloped lips 74 and 75 are arranged out of phase in a circumferential direction, any number of sloped lips crossing in a sea flag wall shape may be arranged.

The sloped lips 74 and 75 constitute a V-shape 76. Since the sloped lips 74 and 75 are continuous on the outer surface of the cylindrical body the above annular lip is not required. At all the lower V-shapes 76, recesses 77 introducing a medicine liquid as indicated by dotted line may be formed to use the sliding valve as an intermediate valve. The sloped lips 74 and 75 crossing in the shape of a sea slug wall makes the warping of the lips 74 and 75 uniform over the entire circumference. In addition, the V-shape 76 provides capabilities of insertion and linear advancement so that inclination of the sliding valve can be prevented.

FIG. 13 shows an kit style syringe 78 using the above sliding valves. This example uses the first example of FIG. 3 as a front sliding valve 21, the sixth example of FIG. 9 as an intermediate sliding valve and the second embodiment of FIG. 5 as a rear sliding valve (piston), respectively.

The front sliding valve 21 is inserted horizontally with no inclination within a cylinder 79 by the action of the wavy lip (wavy sloped lip) 24 to hold the liquid face of a first medicine liquid 80 at a normal position. For this reason, where the conventional intermediate sliding valve (annular lip type) is used, a medicine liquid does not overflow to the outside of the sliding valve to create smudges and air is not mixed into the cylinder. Since no air is mixed, no vacteria is mixed. In this example, since the intermediate sliding valve 56 has openings 61, 62 and a gap 63 among sloped lips 57–60, the medicine liquid 80 intrude among the sloped lips 57–60 to remove air stagnancy, thereby assuring safety of a human body and preventing intrusion of vacteria.

Since the intermediate sliding valve 56 is fit straight with no inclination by the action of the sloped lips 57–60, like the front sliding valve 21, to stabilize the liquid surface of the second liquid 81, overflow of the medicine liquid to the outer surface of the rear sliding valve 29 and mixing of air into the cylinder can be prevented. Since the rear sliding valve 29 is also fit straight by the action of the wavy lips 30, 31, the medicine liquid 81 will not overflow to the outside of the sliding valve 29.

Additionally, the sliding valves used should not be limited to those shown in FIG. 13, but may be any one adopted in the examples described above as necessity requires. The syringe should also be not limited to the kit-style syringe 78, but may be a barrel-style syringe or a glass integral style cylinder. The medicine liquid may be injected in the manner of a single layer (single injection) or plural layers (separate injection).

It should be noted that the kit-style syringe 78 shown in FIG. 13 has been proposed in the application of PCT/JP94/2138 filed by the applicant of the present application.

As described above, in the sliding valve (claim 6–13) for a syringe according to the present invention, when the sliding valve is fit in the cylinder, since the sloped lips have sliding areas for the inner surface of the cylinder over its substantially entire length, the rigidity of the sliding valve made of an elastic material on the sliding face is enhanced. This makes warping deformation over the entire periphery of the lips uniform as compared with the conventional valve equipped with only the annular lip. In addition, the V-shape of the wavy sloped lips and the edge action of an inverted ι\ stabilizes capabilities of insertion and linear advancement for the cylinder. Thus, the sliding valve can be inserted horizontally into the cylinder, thus preventing overflow of the medicine liquid to the outside of the sliding valve and mixing of air (vacteria) into the cylinder. By using the sliding valve defined in claims 8, 9, 11 and 12 as an intermediate sliding valve, the medicine liquid is filled between the sloped lips and between the sloped lips and annular lip, thereby preventing air stagnancy on the outside of the sliding valve, i.e., intrusion of vacteria.

Embodiment 3

Figure 14:
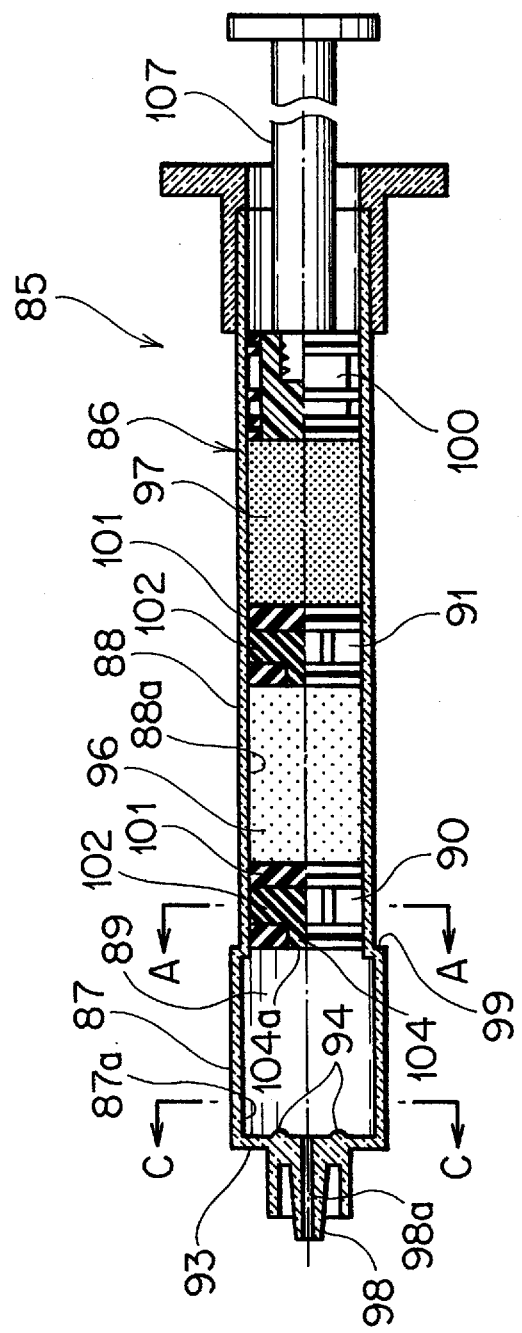
FIG. 14 is a longitudinal sectional view showing a kit-style syringe having a simple structure according to the present invention.
Figure 15:
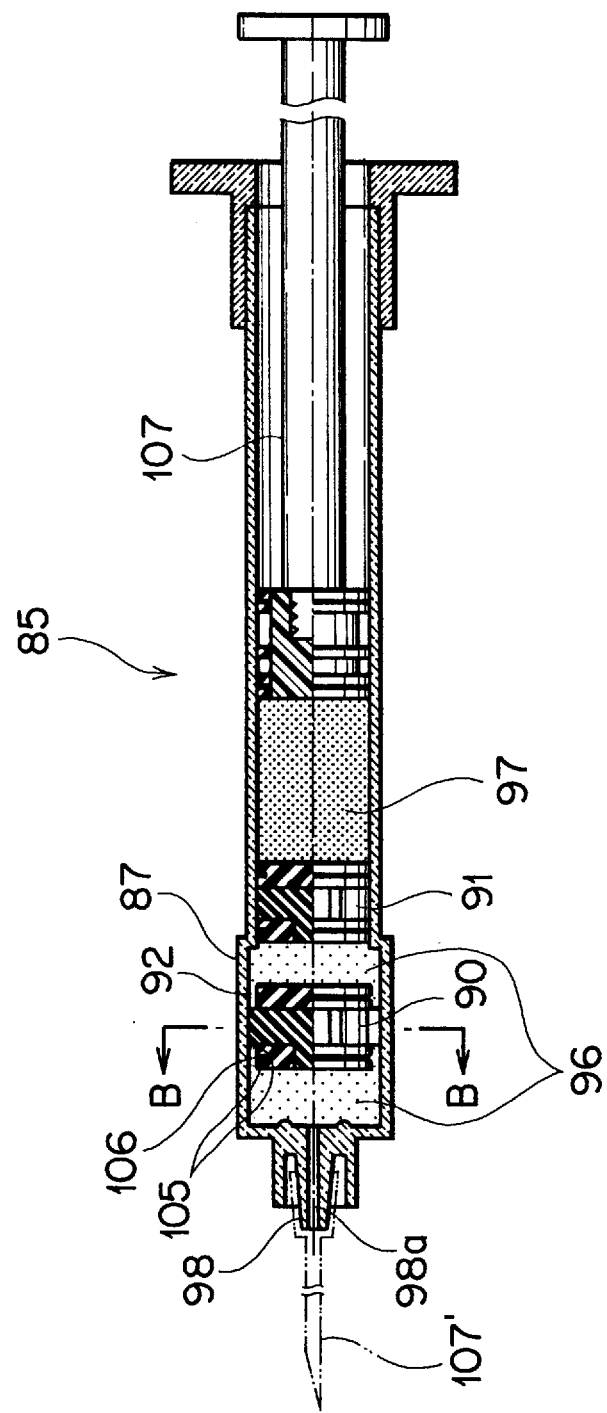
FIG. 15 is a longitudinal sectional view showing the state where a first medicine liquid has been discharged in the kit-style syringe according to the present invention.
Figure 16:
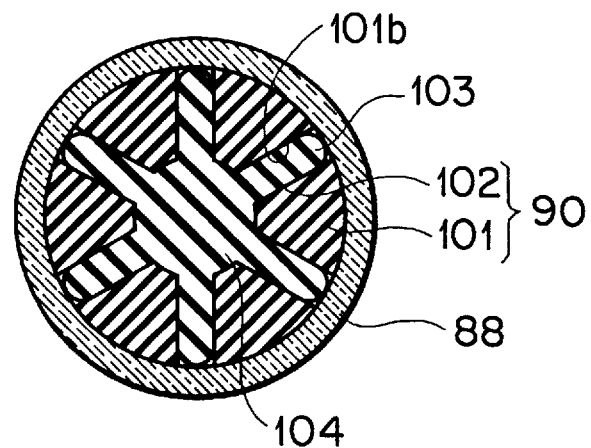
FIG. 16 is a sectional view taken in line A—A of FIG. 14.
Figure 17:
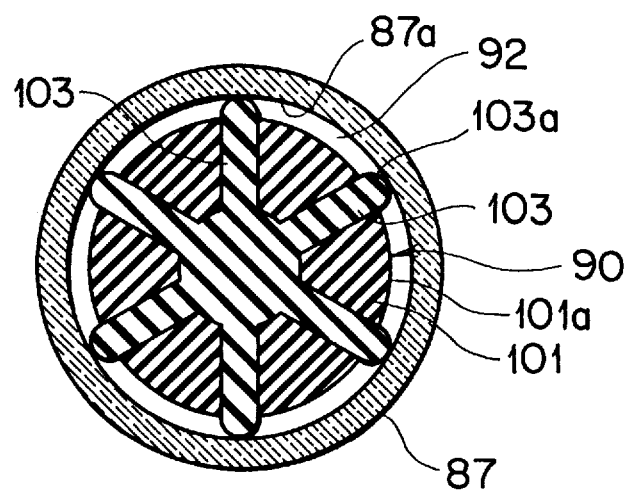
FIG. 17 is a sectional view taken in line B—B of FIG. 15.

FIGS. 14 to 23 show one embodiment of the syringe according to the present invention. As shown in FIG. 14, a syringe 85 includes a cylinder 86 and a bulging portion 87 having a relatively large inner diameter area 87a at the front end thereof and integral thereto. Within a space 89 having a sectional disk-shape in the bulging portion 87, sliding valves 90, 91 in the cylinder 86 can be accommodated with a gap 92 from the outer face area of the valves (FIGS. 15 and 17). A plurality of supporting protrusions 94 are provided on the bottom wall 93 of the bulging portion 87 so that the medicine liquids 96 and 97 within the cylinder 86 can be guided into an inner hole 98a of a syringe needle connection portion 98 successive to the bulging portion 87, through the gap 92 and a gap 95 (FIG. 22) formed by the protrusions 94.

The cylinder 86 may be made of glass, most preferably synthetic resin material such as amorphous polyolefin with high moldablity and capable of providing a mirror-face. The syringe using a cylinder of amorphous polyolefin has been already proposed in the application of PCT/JP94/2138 by the applicant of this application.

In this embodiment, the exterior of the bulging portion 87 integral to the cylinder 86 is made so as to have a diameter larger than the inner diameter of the straight portion 88 of the cylinder 86. But, the inner diameter 87a of the bulging portion 87 has only to be larger than the inner diameter of the straight portion 88. The outer diameter of the bulging portion 87 may be equal to that of the straight portion 88. In this embodiment, the outer wall of the bulging portion 87 is successively integral to that of the straight portion 88 through an annular step 99.

The bulging portion 87 can be easily formed by the molding method described later (FIGS. 26–28).

In this embodiment, within the straight portion 88 of the cylinder 86, two sliding valves (front stopper 90 and middle stopper 91) are arranged to constitute a kit-style syringe 85 in a series separate injection type. As seen from FIG. 14, the front sliding valve 90 is positioned at a position slightly rear of the bulging portion 87 within the straight portion 88, whereas the intermediate sliding valve 91 is substantially located in the middle of the straight portion 88. A first medicine liquid 96 is filled between the front sliding valve 90 and the intermediate sliding valve 91 whereas a second medicine liquid 97 is filled between the intermediate sliding valve 91 and the rear plunger (end stopper) 100. For example, the first medicine liquid 96 may be local anesthesia and the second medicine liquid 97 may be hyaluronic acid sodium which is medicine for knee-joint arthritis to relax pain of a patient when the medicine is given to him.

Figure 18:
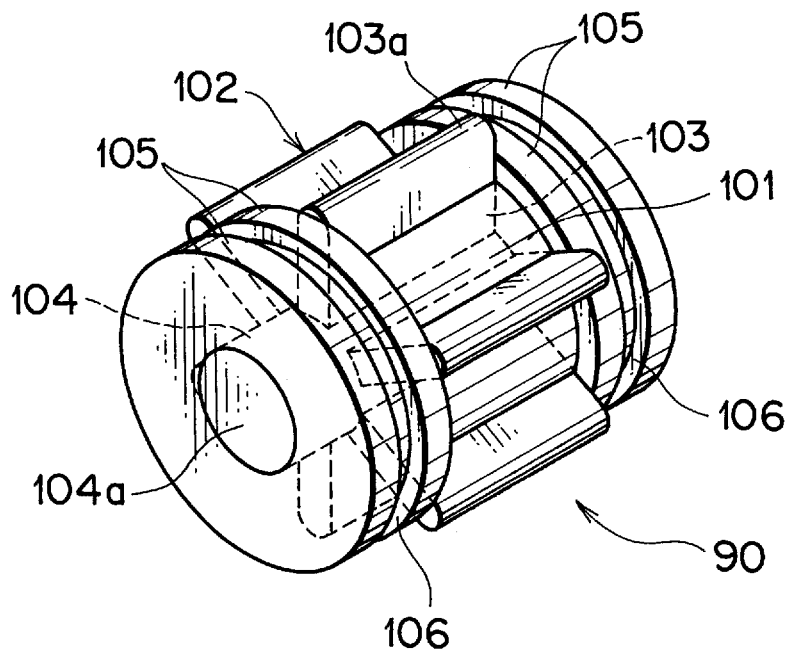
FIG. 18 is a perspective view showing a sliding valve composed of two members.

As shown in FIGS. 16 to 18, each of the sliding valves 90 and 91 is made of two different rubber materials (main body 101 and supporting member 102). For this reason, when the sliding valve 90 is advanced into the bulging portion 87 from the straight portion 88 of the cylinder 86, a part 103 of the rubber member (supporting member) 102 which is soft and apt to expand and contract protrudes in a radial direction, thereby supporting the sliding valve 90 within the bulging portion 87 of the cylinder 86 with no shakiness so that the gap 92 is maintained uniform.

In FIG. 16, the one rubber member (supporting member) 102 is incorporated into the straight portion 88 of the cylinder 86 with a higher contraction coefficient than that of the main body 101. As shown in FIG. 17, when the sliding valve 90 is substantially opened, the supporting member 102 expands to a larger extent than the main body 101. The front sliding valve 90 and the intermediate sliding valve 91 have the same structure so that the sectional shape and operation of the intermediate sliding valve 91 is the same as explained in FIGS. 16 and 17.

The main body 101 is generally formed of a short cylindrical body. The supporting body 102 includes a central portion 104 having a disk shape located at the center of the main body 101 and a plurality of fin-shaped elastic portions (protruding portions) 103 extending in a radial direction therefrom into the main body.

As shown in FIG. 17, the tips 103a (supporting protrusion) of each elastic portion 103 protrudes outwardly from the outer surface of the main body 101 in a free state to be brought into contact with the inner surface 87a of the cylinder bulging portion 87. The supporting protrusion 103a is formed of a sectional semi-circular shape and brought into contact with the inner face of the cylinder 86 with low sliding resistance.

As shown in FIG. 18, each elastic portion 103 of the supporting member 102 is located in the middle of the body 101 in an axial direction. The elastic portion 103 is formed of a rectangular plate shape in which its length in the axial direction is longer than its thickness. Each of both ends of the main body 101 has annular lips 105 which are in a slidable contact with the inner surface of the cylinder straight portion 88 and an annular groove 106 interposed therebetween (FIG. 15). The center portion 104 (FIG. 14) of the supporting member 101 is extended like a boss toward one sense of the axial direction so that the tip 104a of the center portion 104 is exposed. The outer diameter of the middle portion of the body 101 is slightly smaller than that of the annular lips 105 at both ends.

The main body 101 is made of a material which is hard enough to provide a small amount of deformation and is difficult to expand or extract. On the other hand, the supporting member 102 is made of a material which is soft enough to provide a large amount of deformation and is apt to expand/extract to have an elastic modulus equal to or larger than that of the main body 101 (The elasticity means the property of a material that the material having changed its form or volume because of the force applied externally is restored to an original state when the force is removed). Namely, the supporting member is made of the material having lower elastic modulus (higher compressibility) than that of the body 101. The main body 101 is in intimate contact with the supporting member 102.

For example, the main body 101 may be made of polyurethane, and the supporting member 102 may be made of synthetic rubber. For information, the polyurethane has a longitudinal elastic modulus (rate of stress to distortion within a limit of elasticity) of 70–700 Kgf/mm, and the synthetic resin has that of 5–30 Kgf/mm. It should be noted that these numerical values were measured assuming that these materials are isotropic, but not taking the format actually used or direction of external force. As for the elasticity, the main body 101 has a higher elastic modulus whereas the supporting member 102 has a lower elastic modulus. Incidentally, the supporting member 102 may be made of a material with high compressibility such as a porous material (with no coupling of pores). The body 101 and the supporting member 102 may be made of the same material as long as they have different compressibilities (elasticities).

The sliding valves 90 and 91 can be made by insert molding, which is known in the field of e.g. injection molding, in such a manner that the body 101 is first formed by molding, and is inserted in another mold where the supporting members 102 are injection-molded.

Upon completion of the molding, the body 101 and the supporting members 102 are in intimate contact with each other. In this case, as shown in FIG. 16, each of the elastic portions 103 of the supporting members 102 is contracted by the inner wall of the cylinder straight portion 88, a portions of the elastic portion 103 moves along the side wall 101b of the body 101 to retract inwardly in the radial direction. The outer periphery (inner lip portions 105) of the body 101 is brought into contact with the inner face 88a of the cylinder straight portion 88 so that a medicine liquid 96 is sealed as shown in FIG. 14. The front sliding valve 90 serves to separate the medicine liquid 96 from the space 89 within the bulging portion 87 to prevent vacteria from intruding into the medicine liquid.

When the sliding valve 90 comes in the cylinder bulging portion 90 as shown in FIG. 15, the elastic portion 103 protrudes outwardly from the body 101 in the radial direction because of its high elastic modulus so that the sliding valve 90 is supported by the bulging portion 87. The body 101 also expands outwardly because of its elasticity. But, since the inner diameter of the cylinder bulging portion 87 is designed to be larger than the outer diameter of the body 101 of the sliding valve in a free state, a gap is formed between the adjacent elastic portions 103 to introduce the medicine liquid between the cylinder bulging portion 87 and the sliding valve body 101.

The gap 92 may be 0.1–0.5 mm for example. The tips (supporting protrusion) 103a of the elastic portions 103 which expand radially maintain the gaps 92 constant over the circumference to make the flow rate and flow speed of the medicine liquid 96 constant and stabilize the operation force of the plunger rod 107 (FIG. 14). The number of the elastic portions may be at least 3. Provision of six elastic portions in this example can surely stabilize the posture of the sliding valve 90 in the bulging portion 87.

In FIG. 15, the first medicine liquid 96 passes through the gaps 92 on the outside of the front sliding valve 90 and is discharged from the inner hole 98a of the syringe connection portion 98 into the syringe needle 107'.

Figure 19:
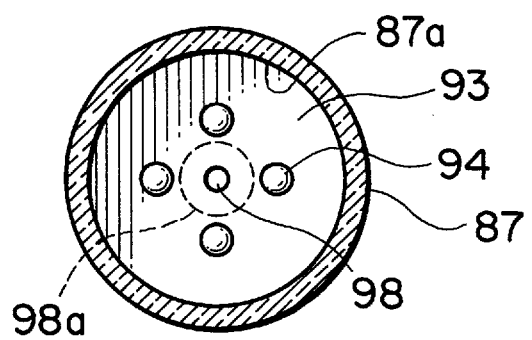
FIG. 19 is a sectional view taken in line C—C of FIG. 14.

FIG. 19 is a sectional view taken in line C—C showing supporting protrusions 94 integrally formed on the bottom wall of the cylinder bulging portion 87.

The protrusions 94 serve to abut on the front of the front sliding valve 90 to form a gap 95 in the radial direction for discharging the medicine liquid between the front sliding valve 90 and the bottom wall of the bulging portion 87. These protrusions are formed at approximate intermediate positions between the inner hole 98a of the syringe connection portion 98 and the inner wall of the cylinder bulging portion 87. In this example, four protrusions 94 are provided at regular intervals to permit the front sliding valve 90 to be supported stably. At least three protrusions 94 are required, and the height of each protrusion 94 may be approximately 1 mm.

Figure 20:
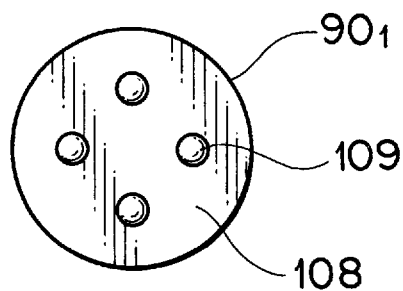
FIG. 20 is a plan view of a front sliding valve having a supporting protrusion.
Figure 21:
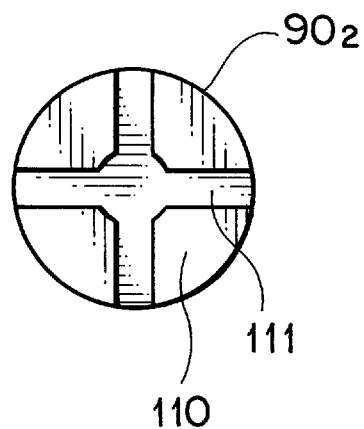
FIG. 21 is a plan view of a front sliding valve having a groove for withdrawing a medicine liquid.

In place of provision of the protrusions on the cylinder side of the bottom of the bulging portion 87 as shown in FIG. 20, plural supporting protrusions 109 may be formed on the front face 108 or both faces of the front sliding valve $90_1$. Further, in place of the protrusions 109, as shown in FIG. 21, a groove 111 for discharging the medicine liquid which communicates with the inner hole 98a of the syringe needle connection portion may be formed on the front end wall 110 or both end walls of the front sliding valve $90_2$. A radial groove (not shown) as in the prior art may be formed on the bottom wall 93 of the cylinder bulging portion 87. But it should be noted that provision of such a radial groove requires relatively high cost.

Figure 22:
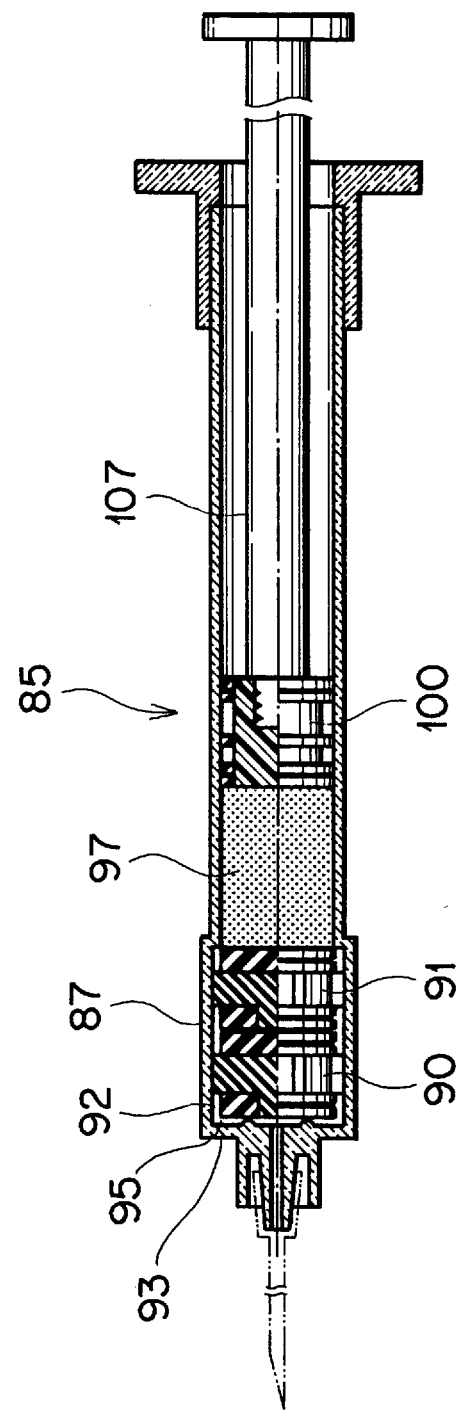
FIG. 22 is a longitudinal sectional view showing the state where the first medicine liquid has been discharged.

FIG. 22 shows the state where the plunger rod 107 is further pushed from the state of FIG. 15 to complete the discharge of the first medicine liquid and the intermediate sliding valve 91 is advanced into the bulging portion 87 to start the discharge of the second medicine liquid 97.

As described above, like the intermediate sliding valve 91, the intermediate sliding valve 91 has the supporting member 102 supported within the body 101. The second medicine liquid 97 passes through the gaps in an axial direction between the respective bodies of the intermediate sliding valve 91 and the front sliding valve 90 and the cylinder bulging portion 87, and is discharged through the gap 95 on the bottom wall 93 of the bulging portion 87.

Figure 23:
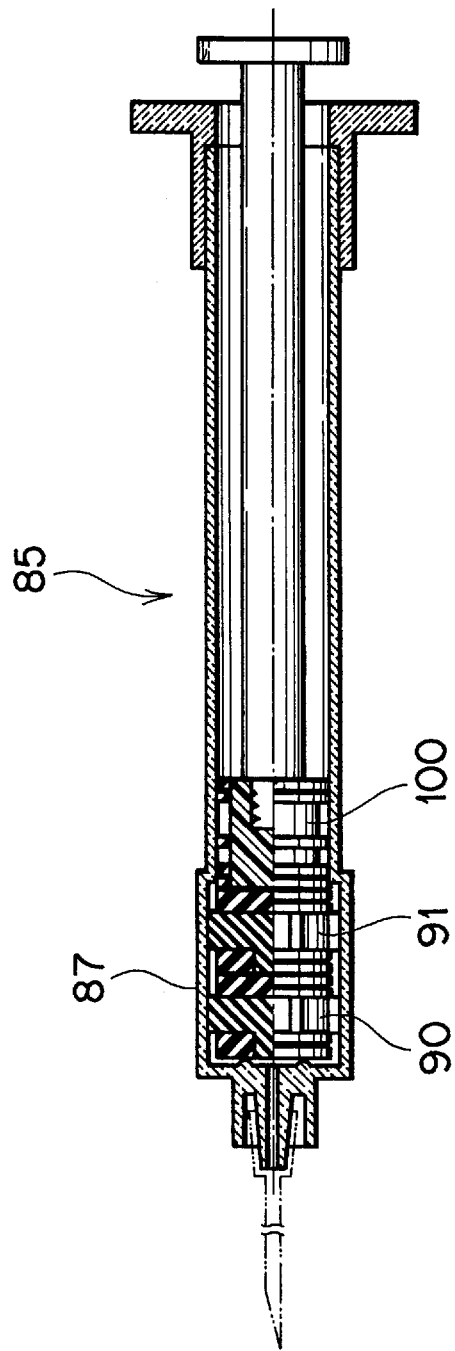
FIG. 23 is a longitudinal sectional view showing the state where the second medicine liquid has been discharged.

FIG. 23 shows the state where the second medicine liquid 97 has been already discharged. In this state, two sliding valves 90 and 91 are housed within the cylinder bulging portion 87, and the plunger 100 abuts on the intermediate sliding valve 91 to stop.

Figure 24:
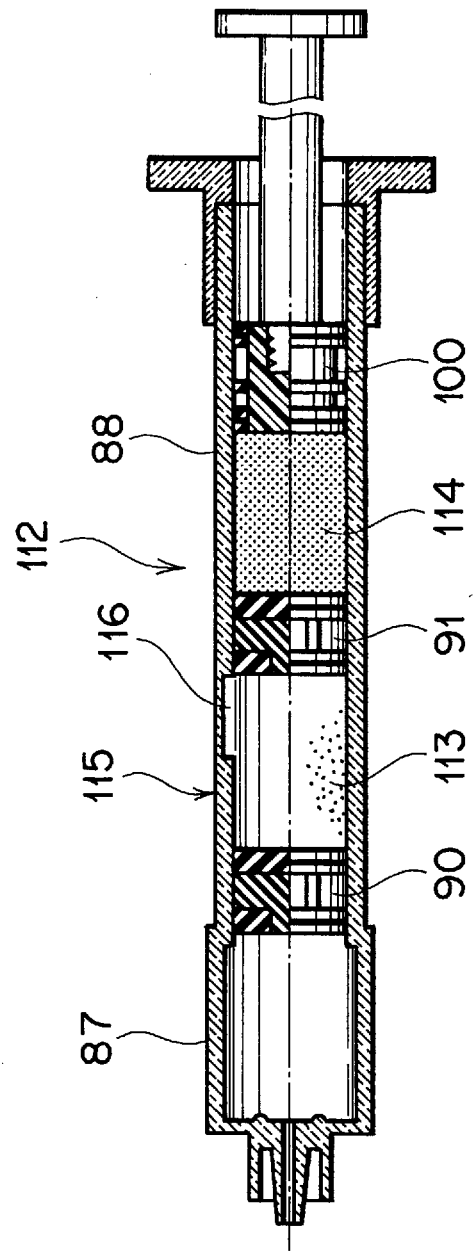
FIG. 24 is a longitudinal sectional view of a syringe of a type in which a medicine is solved as necessity requires to which an integral cylinder is applied.

The examples of the syringe described above relate to the structures of the separate-injection style syringe using the plural sliding valves. The syringe according to the present invention, however, can be applied to not only the separate-injection style syringe, but also an ordinary kit-style syringe which injects a single liquid using a single sliding valve (front stopper 90) or a kit-style syringe 112 which solves medicine as necessity requires as shown in FIG. 24.

In the syringe 112 which solves medicine as necessity requires, powdery medicine 113 is put between the front sliding valve 90 and the intermediate sliding valve 91, and a medicine liquid 114 is filled between the intermediate sliding valve 115 and the plunger 100. The cylinder 115, which is made of synthetic resin such as amorphous polyolefin, has a bulging portion 87 formed at its tip portion, and a bypass groove 116 which is formed on the inner side of the intermediate portion of the straight portion 88 of the cylinder 115. Such a bypass groove 116 has been previously proposed in PCT/JP94/2138. In place of the bypass groove 116, the bulging portion 87 as described above may be formed at the intermediate portion of the cylinder straight portion 88.

In each of the above examples of the syringe, with no supporting member 102 provided on the sliding valves 90 and 91, the medicine liquids 96 and 97 can be discharged from the gaps 92 on the outside of the sliding valves 90 and 91 having advanced into the cylinder bulging portion 87. In this case also, the inner diameter of the bulging portion 87 must be larger than the outer diameter of each of the sliding valves 90 and 91 in the free state.

Figure 25:
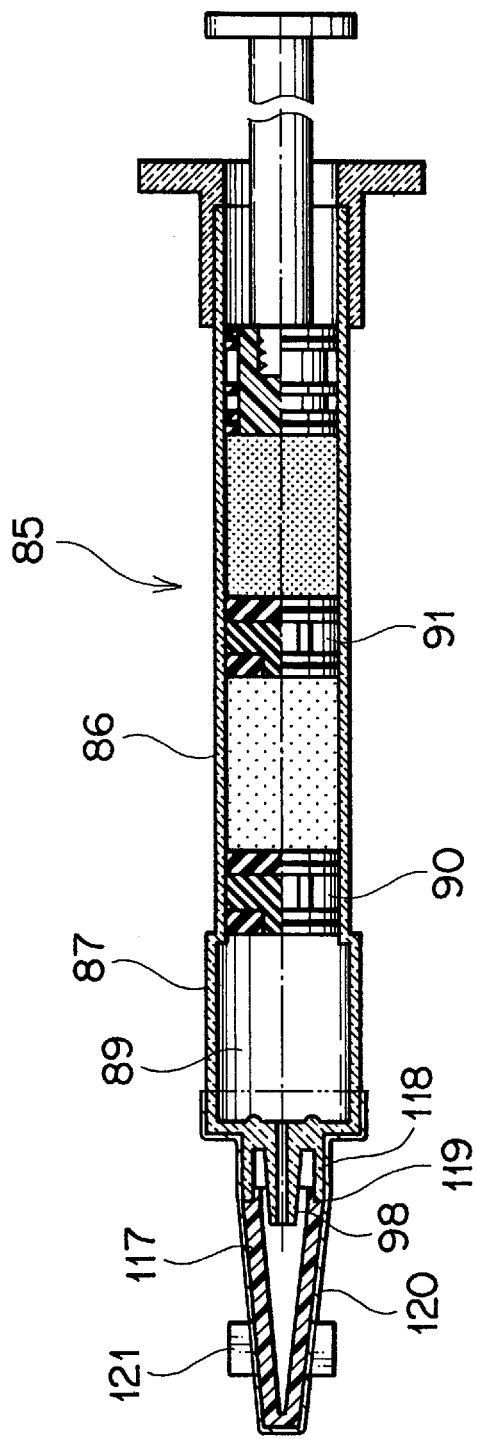
FIG. 25 is a longitudinal sectional view of a syringe according to the present invention in which a fitting portion of a cap is covered with a seal peel.

FIG. 25 shows a syringe structure in which a cap 117 covering the syringe needle connection portion 98 is mounted at the tip of the cylinder 86 of the syringe 85 shown in FIG. 14, and a resin film (seal peel) 120 for preventing intrusion of water and vacteria is formed by dipping on the tip side of the syringe inclusive of the fitting portion 119 between the outer annular protection cylinder 118 of a syringe needle connection portion 98 and a cap 117.

The cap 117 includes a conventional cap and a pair of twisting plates 121 added thereto. By rotating the cap 117 using the twisting plates 121, the resin film 120 can be easily broken. With no twisting plates 121, the cap 117 is simply twisted to break the resin film 120. The twisting plates 121 has been proposed for the cylinder-integral tip sealing portion covering the syringe needle connection portion 98 in the prior application PCT/JP94/2138.

The cap 117 having a hollow longitudinal shape in this example and serving as the tip sealing portion can be provided integrally to the protection outer cylinder 118 at the tip of the cylinder bulging portion 87 by resin molding. With no twisting plate 121, the cap (tip sealing portion) 117 can be simply twisted to break the resin film from the boundary between the cap and the protection outer cylinder 118.

FIGS. 26 to 27 explain an example of a method of molding the cylinder using synthetic resin as a material.

Figure 26B:
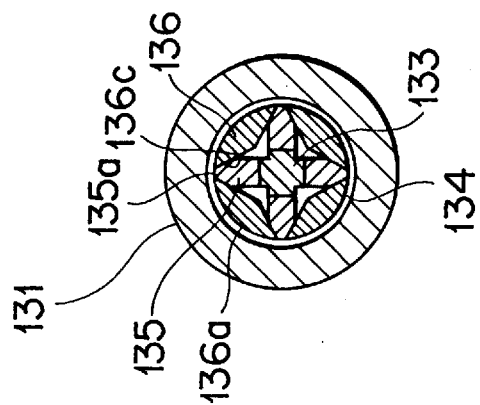
FIG. 26(b) is a sectional view taken in line $D_1$—$D_1$ of FIG. 26(a).
Figure 26A:
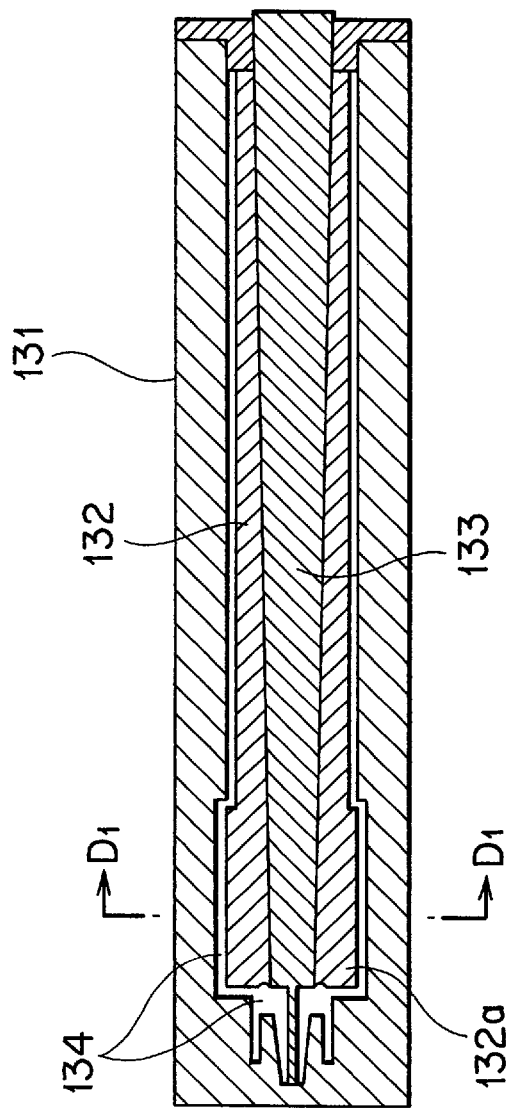
Figure 29:
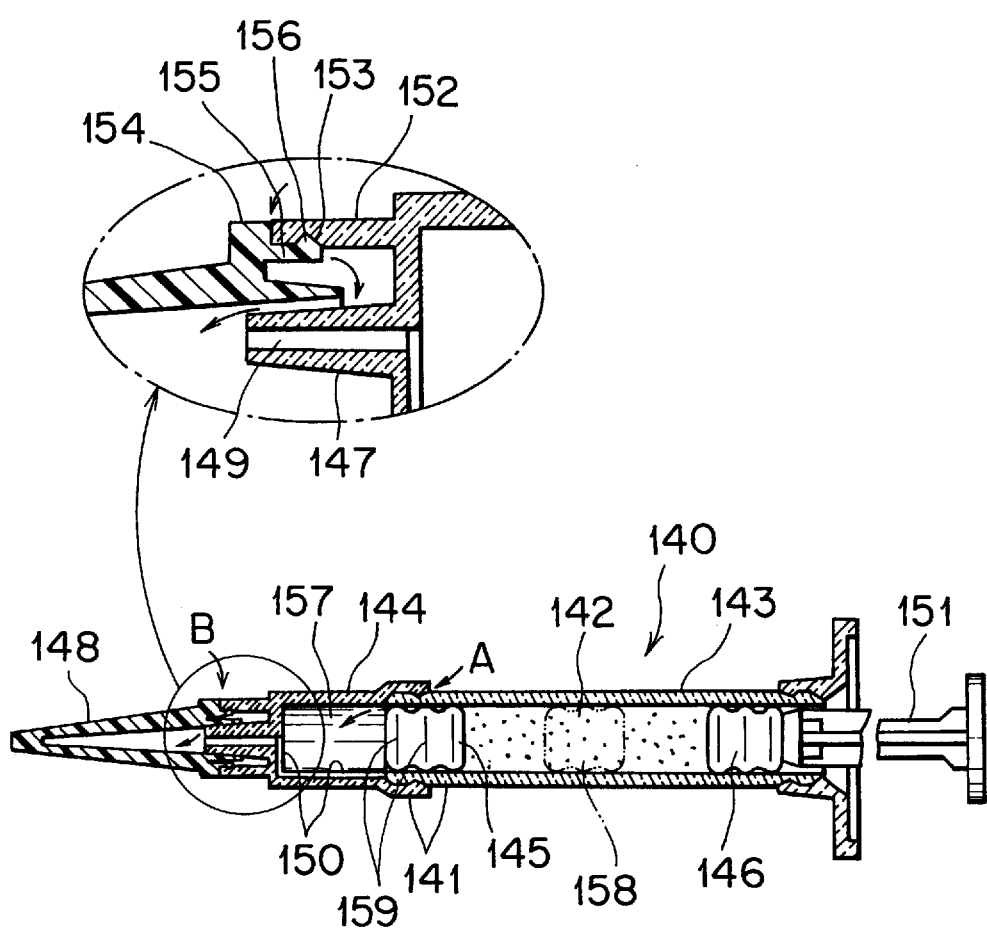
FIG. 29 is a longitudinal sectional view of a prior art syringe (enlarged within a circle).
Figure 31:
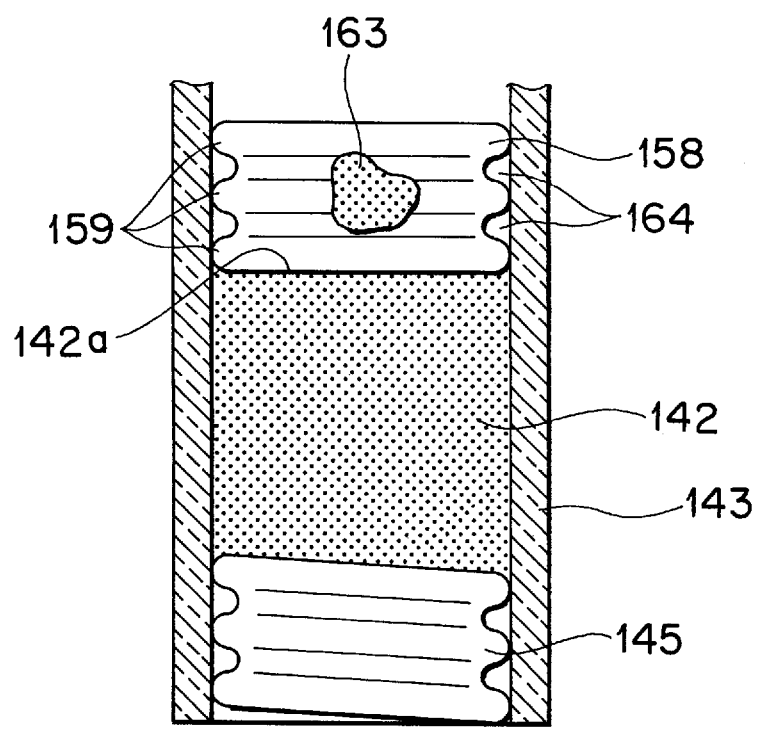
FIG. 31 is a longitudinal sectional view for explaining the problems of the prior art sliding valve.

This method forms the bulging portion 87 in the cylinder 86 using a divisional outer mold 131, a contractible inner mold 132 arranged inside the outer mold 131 and a tapered core 133 to be slid within the inner mold 132. In FIG. 26(a), a cylindrical gap 134 is formed between the outer mold 131 and the inner mold 132, and the resin material is injected into the gap 134. At the larger diameter portion 132a corresponding to the bulging portion 87, as shown in FIG. 26(b), the inner mold 132 is provided with supporting areas 135 each having a substantially triangular or trapezoidal shape and fan-like split molding portions 136 with the tapered faces 136c each supported by the corresponding supporting portion 135. Each supporting portion 135 is supported by the core 133. The split molding portion 136 has an arc face 136a constituting the inner face of the cylinder. The supporting portion 135 has an arc face 135 constituting a portion of the inner face of the cylinder between the adjacent split molding portions 136.

As shown in FIGS. 27(a) and 27(b), after the gap 134 is filled with the resin in a cylindrical shape, when the core 133 is pulled out, the supporting portions 135 and split molding portions 136 contract together. Thus, a gap 137 is created between the bulging portion 87 of the cylinder 86 and the outer portion 132a of the inner mold 132 so that the step 136b of the inner mold 132 escapes from the step 99 of the bulging portion 87. As a result, the inner mold 132 is pulled out. The outer mold 131 is divided to complete a resin-integral cylinder 86. Incidentally, in FIG. 26(a), if the protrusions 94 (FIG. 14) on the bottom of the cylinder are formed at the positions corresponding to the core 133, interference when the inner mold 132 is contracted can be obviated.

FIGS. 28(a) to (f) show a method of molding a cylinder using glass material.

First, as shown in FIG. 28(a), a glass rod 122 as a raw material is heated red. Next, as shown in FIG. 28(b), the glass rod 122 is inserted in a cylindrical mold and a punch 124 is inserted into the rod 122 from the one end of the mold. As seen from FIG. 28(c), the punch 124 is inserted to reach a predetermined distance to make a pre-molding product (blind tube) 125. As seen from FIG. 28(d), the blind tube 125 thus pre-molded is removed from the mold 123 and mounted into a product mold 126. The product mold 126 has a bulging 127. As seen from FIG. 28(e), using a blow nozzle 128 inserted, glass 129 is deposited on the inner face of the mold 126 by air at high pressure. Thus, the bulging portion 87 of the cylinder having a step 99 is formed. Finally, the mold 126 is divided to take out the product 129.

Such a method is known. The syringe needle connection portion is formed individually. Incidentally, the bottom constituting the syringe needle connection portion can be opened to insert a terminal partition 27 made of rubber proposed in FIG. 2 of PCT/JP94-2138.

As described above, in comparison to the conventional structure in which a barrel is mounted to the cylinder as a separate body, the syringe (claims 14 to 20) according to the present invention has no fear of intrusion of flowing water vapor and vacteria into the cylinder from its intermediate area, and requires a groove for discharging medicine liquid to be formed in the tip of the cylinder. This simplifies the structure of the syringe and reduce cost required to form the groove.

INDUSTRIAL APPLICABILITY

As described above, in accordance with a syringe, a sealing structure and a sealing method of the syringe and a sliding valve for the syringe according to the present invention, intrusion of flowing water vapor in post-sterilization, air mixing in mounting the syringe and intrusion of vacteria in preservation can be surely prevented. An inexpensive syringe having a simplified structure can be provided. Industrial waste after use can also be easily processed because of its combustibility.

What is claimed is:

1. A method of sealing a syringe to prevent post sterilization intrusion of water vapor and/or bacteria into the interior of the syringe, comprising the steps of:

immersing at least a portion of a syringe including a portion of a barrel and a cap which is seated on the end of the barrel and which covers a syringe needle connection portion, in a liquefied synthetic resin;

lifting the syringe out of the liquefied resin; and allowing a coating of resin on the surface of the syringe to harden and form a hermetic paint-like film over the exterior of the barrel to cover and hermetically seal at least a portion of the syringe barrel and a cap which covers a syringe needle connection portion against the intrusion of water vapor and bacteria.

2. A method of sealing a syringe as set forth in claim 1, wherein the liquefied resin is prepared by fusing a resin, and wherein the step of immersion is carried out by immersing the syringe in the liquefied resin for a period of 1 second or less.

3. A method of sealing a syringe as set forth in claim 1, wherein the liquefied resin is prepared by dissolving a resin in a solvent, and wherein the step of immersion is carried out by immersing the syringe in the liquefied resin for a period of 1 second or less.

4. A method of sealing a syringe as set forth in claim 3, wherein the solvent is an organic solvent.

5. A method of sealing a syringe as set forth in claim 4, wherein the organic solvent is acetone.

6. A method of sealing a syringe as set forth in claim 1, wherein the resin is selected from among the group comprising: polyethylene, vinyl chloride, polyvinyl acetate and polyvinyl acetal.

7. A method of sealing a syringe as set forth in claim 1, wherein the resin has a melting point of 120° C. or above.

8. A method of sealing a syringe as set forth in claim 2, wherein the temperature of the molten resin is maintained in range of 110°–120° C.

9. A method of sealing a syringe as set forth in claim 3, wherein the liquefied resin is maintained at room temperature, and said step of allowing the coating of resin on the surface of the syringe to harden is carried out using an air flow.

10. A method of sealing a syringe as set forth in claim 2, wherein the step of allowing the coating of resin on the surface of the syringe to harden is carried out for a period of 30–60 seconds.

11. A method of sealing a syringe as set forth in claim 3, wherein the step of allowing the coating of resin on the surface of the syringe to harden is carried out for a period of 30–60 minutes.

12. A syringe prepared in accordance with the method of claim 1.

13. A syringe prepared using a method according to claim 2.

14. A syringe prepared using a method according to claim 3.

15. A syringe prepared using a method according to claim 4.

16. A syringe prepared using a method according to claim 5.

* * * * *